US012130420B2

United States Patent
Otterstrom et al.

(10) Patent No.: US 12,130,420 B2
(45) Date of Patent: Oct. 29, 2024

(54) MULTIPLE IMAGING MODALITY LIGHT SOURCE

(71) Applicant: Stryker Corporation, Kalamazoo, MI (US)

(72) Inventors: Gregory G. Otterstrom, Morgan Hill, CA (US); Ajay Ramesh, Pleasanton, CA (US); Hannah Lawrence, San Jose, CA (US); Candice Pack, Campbell, CA (US); Richard I. Palmisano, San Martin, CA (US)

(73) Assignee: Stryker Corporation, Kalamazoo, MI (US)

( * ) Notice: Subject to any disclaimer, the term of this patent is extended or adjusted under 35 U.S.C. 154(b) by 0 days.

(21) Appl. No.: 18/329,563

(22) Filed: Jun. 5, 2023

(65) Prior Publication Data
US 2023/0314788 A1      Oct. 5, 2023

Related U.S. Application Data

(60) Division of application No. 17/454,055, filed on Nov. 8, 2021, now Pat. No. 11,668,922, which is a (Continued)

(51) Int. Cl.
*G02B 23/24* (2006.01)
*A61B 1/00* (2006.01)
(Continued)

(52) U.S. Cl.
CPC ...... *G02B 23/2461* (2013.01); *A61B 1/00105* (2013.01); *A61B 1/00126* (2013.01); (Continued)

(58) Field of Classification Search
CPC ............ G02B 23/2461; G02B 27/1006; G02B 27/141; G02B 23/26; A61B 1/00105; (Continued)

(56) References Cited

U.S. PATENT DOCUMENTS 4,538,062 A   8/1985   Shishido
5,084,612 A   1/1992   Iwasaki et al.
(Continued)

FOREIGN PATENT DOCUMENTS

CN      1870932 A      11/2006
CN    101295102 A      10/2008
(Continued)

OTHER PUBLICATIONS

First Office Action dated Aug. 13, 2013, directed to CN Application No. 200920145842.3; 21 pages.
(Continued)

*Primary Examiner* — Elmito Breval
(74) *Attorney, Agent, or Firm* — Morrison & Foerster LLP

(57) ABSTRACT

A light source includes a first LED to provide light of a first light wavelength spectrum along a first light path; a second LED to provide light of a second light wavelength spectrum along a second light path; a dichroic filter for passing light emitted from at least one of the first LED and the second LED and reflecting light emitted from at least one of the first LED and the second LED; an optical filter movable between a first position in which the optical filter receives light from the first light path and a second position of which the optical filter does not receive light from the first light path; a light output; a controller which is capable of switching the light source between a first mode for providing a first light to the light output and a second mode for providing a second light to the light output.

18 Claims, 27 Drawing Sheets

Related U.S. Application Data continuation of application No. 16/908,648, filed on Jun. 22, 2020, now Pat. No. 11,169,370, which is a division of application No. 15/458,137, filed on Mar. 14, 2017, now Pat. No. 10,690,904.

(60) Provisional application No. 62/321,414, filed on Apr. 12, 2016.

(51) Int. Cl.

| | | |
|---|---|---|
| *A61B 1/06* | (2006.01) | |
| *G02B 27/10* | (2006.01) | |
| *G02B 27/14* | (2006.01) | |
| *H04N 23/56* | (2023.01) | |
| *A61B 90/00* | (2016.01) | |
| *G02B 23/26* | (2006.01) | |
| *H04N 23/50* | (2023.01) | |

(52) U.S. Cl.
CPC .......... *A61B 1/0638* (2013.01); *A61B 1/0646* (2013.01); *A61B 1/0669* (2013.01); *A61B 1/0684* (2013.01); *G02B 27/1006* (2013.01); *G02B 27/141* (2013.01); *H04N 23/56* (2023.01); *A61B 2090/3937* (2016.02); *G02B 23/26* (2013.01); *H04N 23/555* (2023.01)

(58) Field of Classification Search
CPC . A61B 1/00126; A61B 1/0638; A61B 1/0646; A61B 1/0669; A61B 1/0684; A61B 2090/3937; H04N 23/56; H04N 23/555
See application file for complete search history.

(56) References Cited

U.S. PATENT DOCUMENTS

| | | | |
|---|---|---|---|
| 5,093,769 | A | 3/1992 | Luntsford |
| 5,132,526 | A | 7/1992 | Iwasaki |
| 5,269,289 | A | 12/1993 | Takehana et al. |
| 5,636,259 | A | 6/1997 | Khutoryansky et al. |
| 5,717,605 | A | 2/1998 | Komiya et al. |
| 5,842,765 | A | 12/1998 | Cassarly et al. |
| 5,917,883 | A | 6/1999 | Khutoryansky et al. |
| 5,957,834 | A | 9/1999 | Mochida |
| 6,040,940 | A | 3/2000 | Kawasaki |
| 6,193,401 | B1 | 2/2001 | Girkin et al. |
| 6,195,154 | B1 | 2/2001 | Imai |
| 6,485,414 | B1 | 11/2002 | Neuberger |
| 6,549,239 | B1 | 4/2003 | Tao |
| 6,563,632 | B1 | 5/2003 | Schoeppe et al. |
| 6,663,560 | B2 | 12/2003 | Macaulay et al. |
| 6,730,019 | B2 | 5/2004 | Irion |
| 6,876,494 | B2 | 4/2005 | Ishikawa et al. |
| 6,924,490 | B2 | 8/2005 | Natori |
| 7,015,444 | B2 | 3/2006 | Kawano et al. |
| 7,016,053 | B2 | 3/2006 | Moriuchi et al. |
| 7,176,428 | B2 | 2/2007 | Kawano et al. |
| 7,223,986 | B2 | 5/2007 | Natori |
| 7,239,384 | B2 | 7/2007 | Kawano |
| 7,258,663 | B2 | 8/2007 | Doguchi et al. |
| 7,268,938 | B2 | 9/2007 | Kawano et al. |
| 7,304,789 | B2 | 12/2007 | Hirata et al. |
| 7,448,995 | B2 | 11/2008 | Wiklof et al. |
| 7,583,389 | B2 | 9/2009 | Neal et al. |
| 7,609,440 | B2 | 10/2009 | Tanikawa et al. |
| 7,616,330 | B2 | 11/2009 | Neal et al. |
| 7,623,251 | B2 | 11/2009 | Neal et al. |
| 7,661,862 | B2 | 2/2010 | Lee et al. |
| 8,408,704 | B2 | 4/2013 | Tomidokoro et al. |
| 8,892,190 | B2 | 11/2014 | Docherty et al. |
| 9,459,415 | B2 | 10/2016 | Feingold et al. |
| 10,690,904 | B2 | 6/2020 | Otterstrom et al. |
| 11,169,370 | B2 | 11/2021 | Otterstrom et al. |
| 2002/0014595 | A1 | 2/2002 | Sendai et al. |
| 2002/0043636 | A1 | 4/2002 | Kimura |
| 2002/0101643 | A1 | 8/2002 | Kobayashi |
| 2002/0120181 | A1 | 8/2002 | Irion |
| 2002/0168096 | A1 | 11/2002 | Hakamata et al. |
| 2003/0007087 | A1 | 1/2003 | Hakamata et al. |
| 2003/0042493 | A1 | 3/2003 | Kazakevich |
| 2003/0067645 | A1 | 4/2003 | Ibsen et al. |
| 2003/0147254 | A1 | 8/2003 | Yoneda et al. |
| 2003/0169431 | A1 | 9/2003 | Moriuchi et al. |
| 2003/0184661 | A1 | 10/2003 | Yubata et al. |
| 2003/0202090 | A1 | 10/2003 | Ota et al. |
| 2004/0061673 | A1 | 4/2004 | Ishikawa et al. |
| 2004/0105095 | A1 | 6/2004 | Stobrawa et al. |
| 2004/0105482 | A1 | 6/2004 | Sugiyama et al. |
| 2004/0147806 | A1 | 7/2004 | Adler |
| 2004/0228373 | A1 | 11/2004 | Tatsuno et al. |
| 2005/0020926 | A1 | 1/2005 | Wiklof et al. |
| 2005/0099824 | A1 | 5/2005 | Dowling et al. |
| 2005/0187441 | A1 | 8/2005 | Kawasaki et al. |
| 2005/0200947 | A1 | 9/2005 | Hirata et al. |
| 2005/0203423 | A1 | 9/2005 | Zeng et al. |
| 2005/0211872 | A1 | 9/2005 | Kawano et al. |
| 2005/0224692 | A1 | 10/2005 | Tsuchiya et al. |
| 2005/0228231 | A1 | 10/2005 | Mackinnon et al. |
| 2005/0237604 | A1 | 10/2005 | Kawano et al. |
| 2005/0245789 | A1* | 11/2005 | Smith ................. A61B 1/0016 137/560 |
| 2005/0251230 | A1 | 11/2005 | Mackinnon et al. |
| 2005/0253056 | A1 | 11/2005 | Nakata |
| 2005/0270641 | A1 | 12/2005 | Hirata et al. |
| 2005/0276553 | A1 | 12/2005 | Kazakevich |
| 2005/0279950 | A1 | 12/2005 | Kawano et al. |
| 2006/0009682 | A1 | 1/2006 | Nagasawa et al. |
| 2006/0017920 | A1 | 1/2006 | Tsuchiya et al. |
| 2006/0103922 | A1 | 5/2006 | Tsuyuki |
| 2006/0146125 | A1 | 7/2006 | Yamada |
| 2006/0166162 | A1* | 7/2006 | Ting ................. A61B 1/0684 433/29 |
| 2006/0175546 | A1 | 8/2006 | Asai |
| 2006/0187499 | A1 | 8/2006 | Natori et al. |
| 2007/0028918 | A1 | 2/2007 | Tsuyuki et al. |
| 2007/0051869 | A1 | 3/2007 | Knebel |
| 2007/0091425 | A1 | 4/2007 | Kawano |
| 2007/0097369 | A1 | 5/2007 | Shimada |
| 2007/0100241 | A1 | 5/2007 | Adler |
| 2007/0104417 | A1 | 5/2007 | Tanaka et al. |
| 2007/0120070 | A1 | 5/2007 | Kawano et al. |
| 2007/0153367 | A1 | 7/2007 | Kawasaki |
| 2007/0159682 | A1 | 7/2007 | Tanaka et al. |
| 2007/0188707 | A1 | 8/2007 | Nanjo |
| 2007/0213588 | A1 | 9/2007 | Morishita et al. |
| 2007/0213593 | A1 | 9/2007 | Nakaoka |
| 2007/0236701 | A1 | 10/2007 | Neal et al. |
| 2007/0236702 | A1 | 10/2007 | Neal et al. |
| 2007/0236703 | A1 | 10/2007 | Neal et al. |
| 2007/0270652 | A1 | 11/2007 | Morishita et al. |
| 2007/0274649 | A1 | 11/2007 | Takahashi et al. |
| 2007/0299309 | A1 | 12/2007 | Seibel et al. |
| 2008/0039695 | A1 | 2/2008 | Takaoka et al. |
| 2008/0043244 | A1 | 2/2008 | Hatori et al. |
| 2008/0137328 | A1 | 6/2008 | Lee et al. |
| 2008/0186388 | A1 | 8/2008 | Yamagata et al. |
| 2008/0198448 | A1 | 8/2008 | Ganser et al. |
| 2008/0225388 | A1 | 9/2008 | Hirata |
| 2008/0232131 | A1 | 9/2008 | Suda |
| 2008/0246920 | A1 | 10/2008 | Buczek et al. |
| 2008/0252900 | A1 | 10/2008 | Hatori |
| 2008/0283770 | A1 | 11/2008 | Takahashi |
| 2009/0032732 | A1 | 2/2009 | Konishi |
| 2009/0067042 | A1 | 3/2009 | Tanikawa |
| 2009/0073553 | A1 | 3/2009 | Hirata |
| 2009/0201577 | A1 | 8/2009 | Laplante |
| 2009/0244521 | A1 | 10/2009 | Yazdanfar et al. |
| 2009/0251704 | A1 | 10/2009 | Masuda |
| 2010/0245552 | A1 | 9/2010 | Higuchi |
| 2011/0063427 | A1 | 3/2011 | Fengler |
| 2011/0208004 | A1 | 8/2011 | Feingold |
| 2012/0004508 | A1 | 1/2012 | McDowell et al. |
| 2012/0230024 | A1 | 9/2012 | Moore |
| 2012/0248333 | A1 | 10/2012 | Fallert et al. |

(56) References Cited

U.S. PATENT DOCUMENTS

| | | |
|---|---|---|
| 2012/0257030 A1 | 10/2012 | Lim et al. |
| 2014/0031623 A1 | 1/2014 | Kagaya |
| 2015/0098065 A1 | 4/2015 | Tanaka |
| 2015/0112192 A1 | 4/2015 | Docherty et al. |
| 2015/0112193 A1 | 4/2015 | Docherty et al. |
| 2015/0238127 A1 | 8/2015 | Saito |
| 2015/0026789 A1 | 9/2015 | Brukilacchio et al. |
| 2015/0253653 A1 | 9/2015 | Fujita |
| 2016/0022126 A1 | 1/2016 | Ramesh et al. |
| 2016/0029874 A1 | 2/2016 | Usami |
| 2016/0231494 A1 | 8/2016 | Feingold et al. |
| 2017/0188853 A1 | 7/2017 | Nakao |
| 2017/0293134 A1 | 10/2017 | Otterstrom et al. |
| 2021/0011274 A1 | 1/2021 | Otterstrom et al. |
| 2022/0057622 A1 | 2/2022 | Otterstrom et al. |

FOREIGN PATENT DOCUMENTS

| | | |
|---|---|---|
| EP | 1930751 A2 | 6/2008 |
| JP | S54-10237 Y2 | 5/1979 |
| JP | H7-67832 A | 3/1995 |
| JP | H7-275192 A | 10/1995 |
| JP | H11-253384 A | 9/1999 |
| JP | 2001-224015 A | 8/2001 |
| JP | 2006-87764 A | 4/2006 |
| WO | 2005/000110 A2 | 1/2005 |
| WO | 2010/059197 A2 | 5/2010 |
| WO | 2014/152757 A2 | 9/2014 |

OTHER PUBLICATIONS

International Preliminary Report on Patentability dated Jun. 3, 2011, directed to International Application No. PCT/US2009/006155; 10 pages.

International Search Report and Written Opinion mailed Jun. 7, 2010, directed to International Application No. PCT/US2009/006155; 14 pages.

International Search Report mailed Nov. 3, 2014, directed to International Application No. PCT/US2014/027700; 6 pages.

Office Action dated Feb. 28, 2014, directed to JP Application No. 2011-536337; 6 pages.

Office Action dated Jul. 19, 2013, directed to JP Application No. 2011-536337; 7 pages.

Office Action dated Nov. 5, 2020, directed to JP Application No. 2011-536337; 5 pages.

Otterstrom et al., U.S. Office Action dated Sep. 26, 2019, directed to U.S. Appl. No. 15/458,137; 6 pages.

Otterstrom et al., U.S. Office Action dated Feb. 19, 2019, directed to U.S. Appl. No. 15/458,137; 6 pages.

Otterstrom et al., U.S. Notice of Allowance and Fee(s) due mailed Feb. 13, 2020, directed to U.S. Appl. No. 15/458,137; 7 pages.

Otterstrom et al., U.S. Restriction Requirement dated Nov. 5, 2018, directed to U.S. Appl. No. 15/458,137; 5 pages.

International Written Opinion mailed Nov. 3, 2014, directed to International Application No. PCT/US2014/027700; 7 pages.

Otterstrom et al., U.S. Office Action dated Oct. 28, 2020, directed to U.S. Appl. No. 16/908,648; 9 pages.

Otterstrom et al., U.S. Notice of Allowance and Fee(s) Due dated Jul. 2, 2021, directed to U.S. Appl. No. 16/908,648; 8 pages.

Otterstrom et al., U.S. Office Action dated Jun. 15, 2022, directed to U.S. Appl. No. 17/54,055; 8 pages.

Otterstrom et al., U.S. Notice of Allowance and Fee(s) Due mailed Jan. 25, 2023, directed to U.S. Appl. No. 17/54,055; 7 pages.

\* cited by examiner

MULTIPLE IMAGING MODALITY LIGHT SOURCE

CROSS-REFERENCE TO RELATED APPLICATIONS

This application is a divisional of U.S. patent application Ser. No. 17/454,055 filed Nov. 8, 2021, which is a continuation of U.S. patent application Ser. No. 16/908,648, filed Jun. 22, 2020, now U.S. Pat. No. 11,169,370, which is a divisional of U.S. patent application Ser. No. 15/458,137, filed Mar. 14, 2017, now U.S. Pat. No. 10,690,904, which claims the benefit of U.S. Provisional Application No. 62/321,414, filed Apr. 12, 2016, the entire contents of each of which are incorporated by reference herein.

FIELD OF THE INVENTION

The present invention relates generally to a solid state system for providing illumination from an external light source through an instrument to an object, such as a patient surgical site. The external light source includes components for providing light in the visible spectrum as well as light in the ultraviolet and/or infrared spectrums.

BACKGROUND OF THE INVENTION

Endoscopic systems are used to inspect regions within a body during surgery. Endoscopic systems typically include an endoscope, a light source, and an imaging device such as a camera head. Typically, an endoscope includes a rigid or flexible elongated insertion tube equipped with a set of optical fibers that extend from a proximal handle through the endoscope body to a distal viewing tip. An external light source provides light to the optic fibers via a cable that attaches to a post or other structure on the endoscope. The endoscope also receives images and transmits them to the imaging device for providing an image to a monitor or other display apparatus for viewing by a surgeon.

In one commercial embodiment, an endoscopic system includes a solid state light source that generates white light which is conveyed to a distal end of the endoscope via a light guide. The light guide includes multiple fibers and is connected between an output connector of the light source and a light post of the endoscope. The white light illuminates a working area at the distal end of the endoscope. The camera, connected to a handle of the endoscope, generates video signals representative of images at the working area for display on a video monitor.

The light source includes an optical system and a lens array used to collimate light from an LED array. A focusing lens focuses the light onto the light guide. The lenses collect light emitted by LEDs. The lenses may be single lenses, such as single or double aspherics, compound lenses, radiant index type lenses, or combinations of each of these. Other arrangements have lens arrays that are implemented as part of an LED array by adhesion, fusion, or other means. Some arrangements have a rectangular-shaped LED and lens array.

The focal length of the lens and the diameter of the lens are chosen on the order of a few millimeters. The actual values are selected based on the size of the LED emitting surface which determines the field of view of the lens.

The collected light from the lens array travels to a focusing lens. The focusing lens projects the light image of each LED emitting surface onto an entrance face of the light guide. The image is magnified so that the size is approximately equal to the size of the entrance face of the light guide. The light guide transports the light to the endoscope. The light passes through the endoscope to illuminate a surgical site. Light is reflected off of the surgical site which is received by the endoscope and transmitted to the camera head. The camera head provides images of the surgical site for display on the monitor.

Another endoscopic system that has been designed is described in commonly-owned PCT Application No. WO 2010/059197 A2.

The above-described endoscopic systems do not concern themselves with the ability of providing specific wavelengths of light or excitation of fluorescent markers in an object, such as a body part at a surgical site. While there are systems on the market that do provide excitation light for fluorescent markers, these systems typically use incandescent light and/or multiple light sources and multiple components to transmit light to the surgical site, and multiple components to separate the light emitted.

SUMMARY OF THE INVENTION

One embodiment of the present invention includes a single light source which is capable of providing white light, and providing ultraviolet light. The embodiment includes one or more movable light filters to provide a variety of illumination modes.

Another embodiment of the invention employs a light source to provide light in the red, blue, green, ultraviolet and infrared wavelength spectra to an endoscope which transports the light to a surgical site. Reflected light and fluorescent light from fluorescent markers at the surgical site are then transmitted through the endoscope, through a notch filter, for separation of light in the desired spectra, then to the imaging device.

Yet another embodiment of the invention includes two or more infrared laser diodes in the same light engine slot. The two or more infrared laser diodes are each connected to the same heat sink.

Still another embodiment of the invention employs a modular light engine which may be replaced with other modular light engines and/or may provide additional illumination modes to an existing light source.

Other advantages, objects and/or purposes of the invention will be apparent to persons familiar with constructions of this general type upon reading the following specification and inspecting the accompanying drawings.

DETAILED DESCRIPTION

Figure 1:
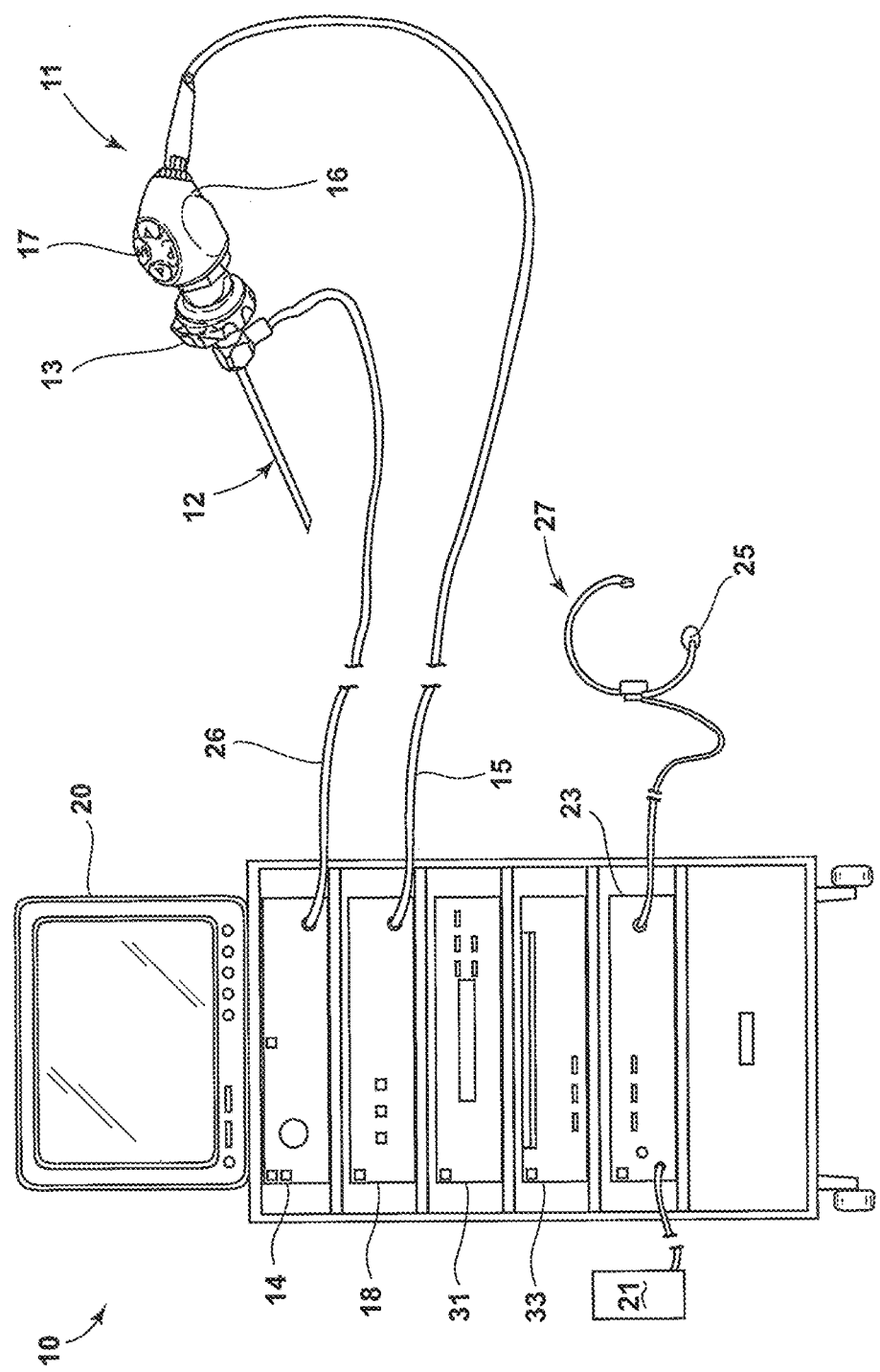
FIG. 1 is an illustration of an endoscopic camera arrangement which is an embodiment of the present invention.

Certain terminology will be used in the following description for convenience and reference only, and will not be limiting. For example, the words "upwardly," "downwardly," "rightwardly," and "leftwardly" will refer to directions in the drawings to which reference is made. The words "inwardly" and "outwardly" will refer to directions toward and away from, respectively, the geometric center of the arrangement, and designated parts thereof. This terminology includes the words specifically mentioned, derivatives thereof, and words of similar import.

FIG. 1 shows an endoscopic camera arrangement 10, including a scope assembly 11 which may be utilized in endoscopic procedures. The scope assembly 11 incorporates an endoscope or scope 12 which is coupled to a camera head 16 by a coupler 13 located at the distal end of the camera head 16. Light is provided to the scope by a light source 14 via a light guide 26, such as a fiber optic cable. The camera head 16 is coupled to a camera control unit (CCU) 18 by an electrical cable 15. The CCU 18 is preferably connected to, and communicates with, the light source 14. Operation of the camera 16 is controlled, in part, by the CCU 18. The cable 15 conveys video image data from the camera head 16 to the CCU 18 and conveys various control signals bi-directionally between the camera head 16 and the CCU 18. In one embodiment, the image data output by the camera head 16 is digital.

A control or switch arrangement 17 is provided on the camera head 16 and allows a user to manually control various functions of the arrangement 10. Voice commands are input into a microphone 25 mounted on a headset 27 worn by the surgeon and coupled to a voice-control unit 23. A hand-held control device 21, such as a tablet with a touch screen user interface or a PDA, may be coupled to the voice control unit 23 as a further control interface. In the illustrated embodiment, a recorder 31 and a printer 33 are also coupled to the CCU 18. Additional devices, such as an image capture and archiving device, may be included in the arrangement 10 and coupled to the CCU 18. Video image data acquired by the camera head 16 and processed by the CCU 18 is converted to images, which can be displayed on a monitor 20, recorded by the recorder 31, and/or used to generate static images, hard copies of which can be produced by the printer 33.

Figure 2:
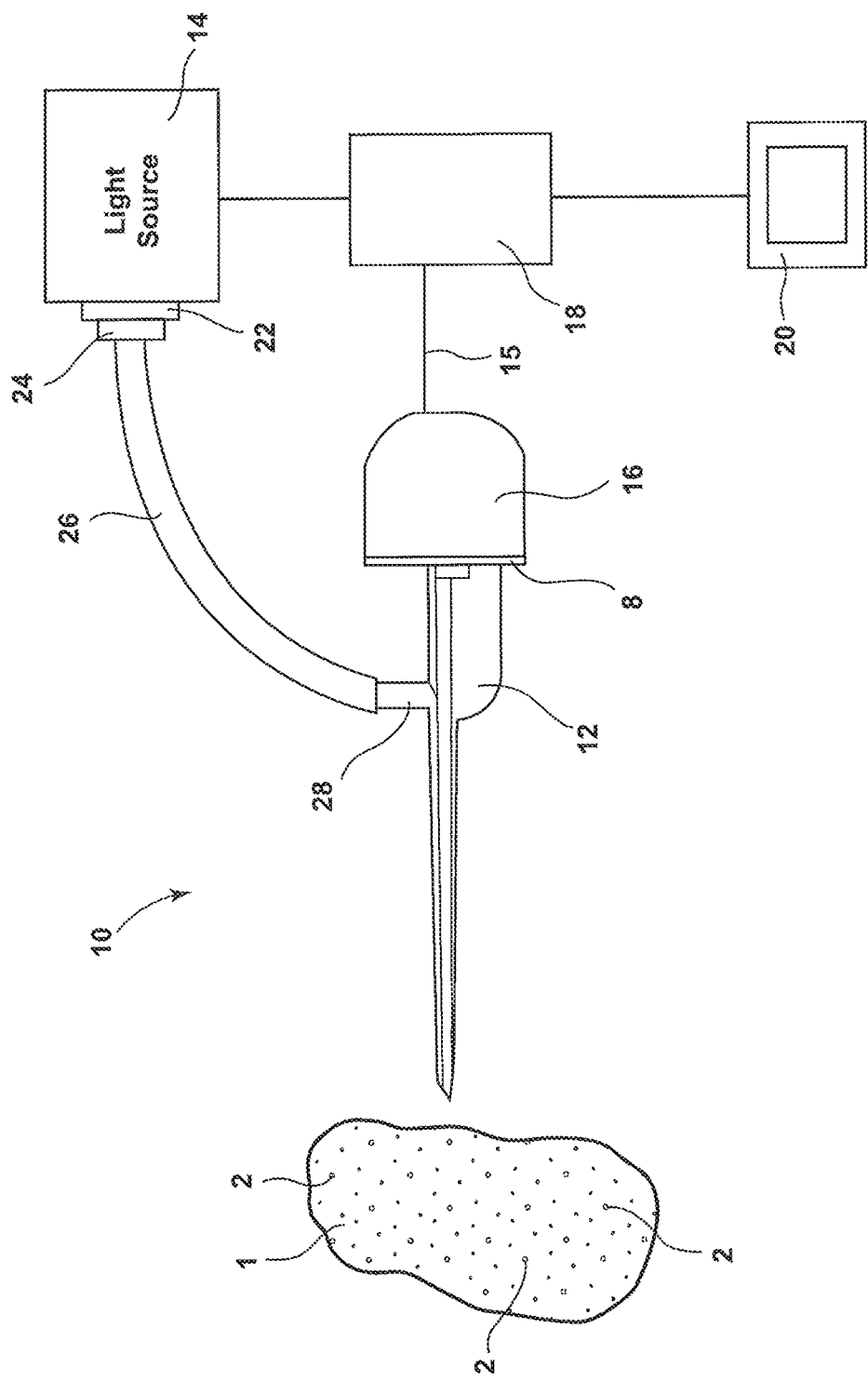
FIG. 2 is a diagram of a portion of the endoscopic camera arrangement of FIG. 1 and an object with fluorescent markers in it.

FIG. 2 shows an embodiment of part of the endoscopic system 10 used to illuminate and receive light from an object 1, such as a surgical site of a patient. The object 1, depending on the procedure, may include fluorescent or other imaging markers 2 therein. The markers 2 are preferably comprised of indocyanine green (ICG) which is an FDA-approved fluorescent dye for bile duct identification and sentinel lymph node (SLN) identification; a hexaminolevulinate hydrochloride imaging agent for locating cancerous tissues such as tumors, also known as UV fluorescent imaging or more specifically, 5-ALA imaging; or a fluorophore such as fluorescein, which is an FDA-approved fluorescent dye for cerebrospinal fluid identification.

Figure 3B:
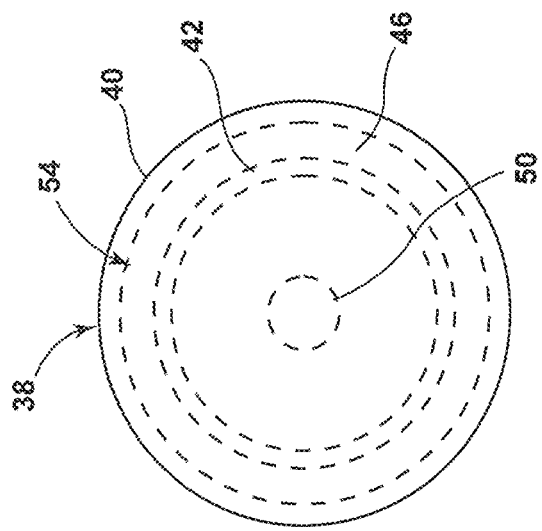
FIG. 3B is an enlarged end view of the distal end of the endoscope as seen generally along line IIIB-IIIB in FIG. 3A.
Figure 3A:
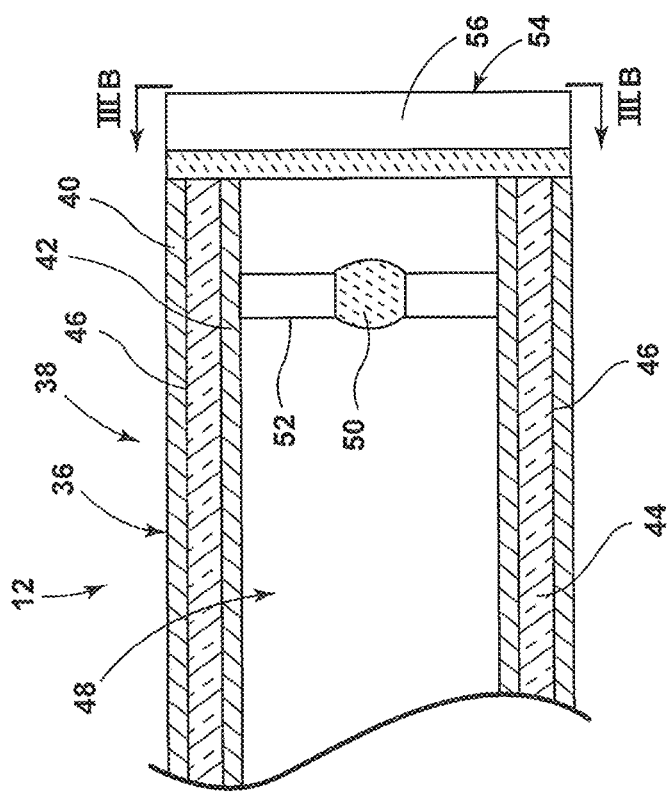
FIG. 3A is an enlarged, longitudinal and fragmentary cross-sectional view of the distal end of a preferred endoscope.

FIGS. 3A and 3B illustrate the structure of a preferred embodiment of the endoscope 12 in greater detail at the distal end 38 thereof. A shaft 36 of the endoscope 12 is defined by a substantially cylindrical and tubular outer housing 40 and an inner tubular housing 42 located within the outer housing 40. The outer and inner housings 40, 42 are sized such that an annular space 44 is defined therebetween which extends along a substantial portion of the longitudinal extent of the shaft 36. A cylindrical optical fiber 46 is located within the annular space 44 and extends from the distal end 38 rearwardly to the proximal end of the endoscope 12 to receive electromagnetic radiation transmitted into the endoscope 12 via the light guide 26.

In the illustrated example, the inner tubular housing 42 encloses the innermost functional components of the endoscope 12, such as an optical train 48. The optical train 48 can comprise an image lens 50 at the distal end 38 suitably fixed or connected to the inner surface of the inner tubular housing 42 with a corresponding generally annular image lens casing 52. A distal window 54 is located at the distal terminus of the tubular outer housing 40, the inner tubular housing 42 and the optical fiber 46. In one embodiment, the otherwise empty spaces in the optical train 48, for instance the space between the image lens 50 and the distal window 54, are hermetically sealed against the exterior of the endoscope 12 and filled with a specified fluid such as low-humidity nitrogen gas. Alternatively, one or more such spaces may be hermetically sealed with respect to the exterior of the endoscope 12 and substantially devoid of fluid. The components and workings of the endoscopic system as described above are conventional and further description is accordingly not provided herein.

The illustrated endoscope 12 includes the distal window 54 on the distal end 38 thereof. The distal window 54 allows the imaging light coming from the optical fiber 46 to pass therethrough for illuminating the surgical field. After passing through the distal window 54, the imaging light reflects off of matter in the surgical field, for example, object 1, and reflects back through and into the endoscope 12 through a center area of the distal window 54 to be passed to an eyepiece. The distal window 54, however, typically does not allow heating light to pass therethrough in order to absorb energy of the heating light to heat the distal window 54. Heating of the distal window 54 prevents moisture from condensating on an exterior surface 56 of the distal window 54, thereby preventing fogging of the endoscope 12. The distal window 54 can comprise an optical absorbing element or an optical absorbing element in combination with another optical element (e.g., a fully transparent window). This endoscope and its anti-fogging features are described in detail in U.S. Ser. No. 14/155,480, that published as U.S. Pub. Pat. App. No. 2014/0200406, and which is hereby incorporated by reference in its entirety.

Figure 4:
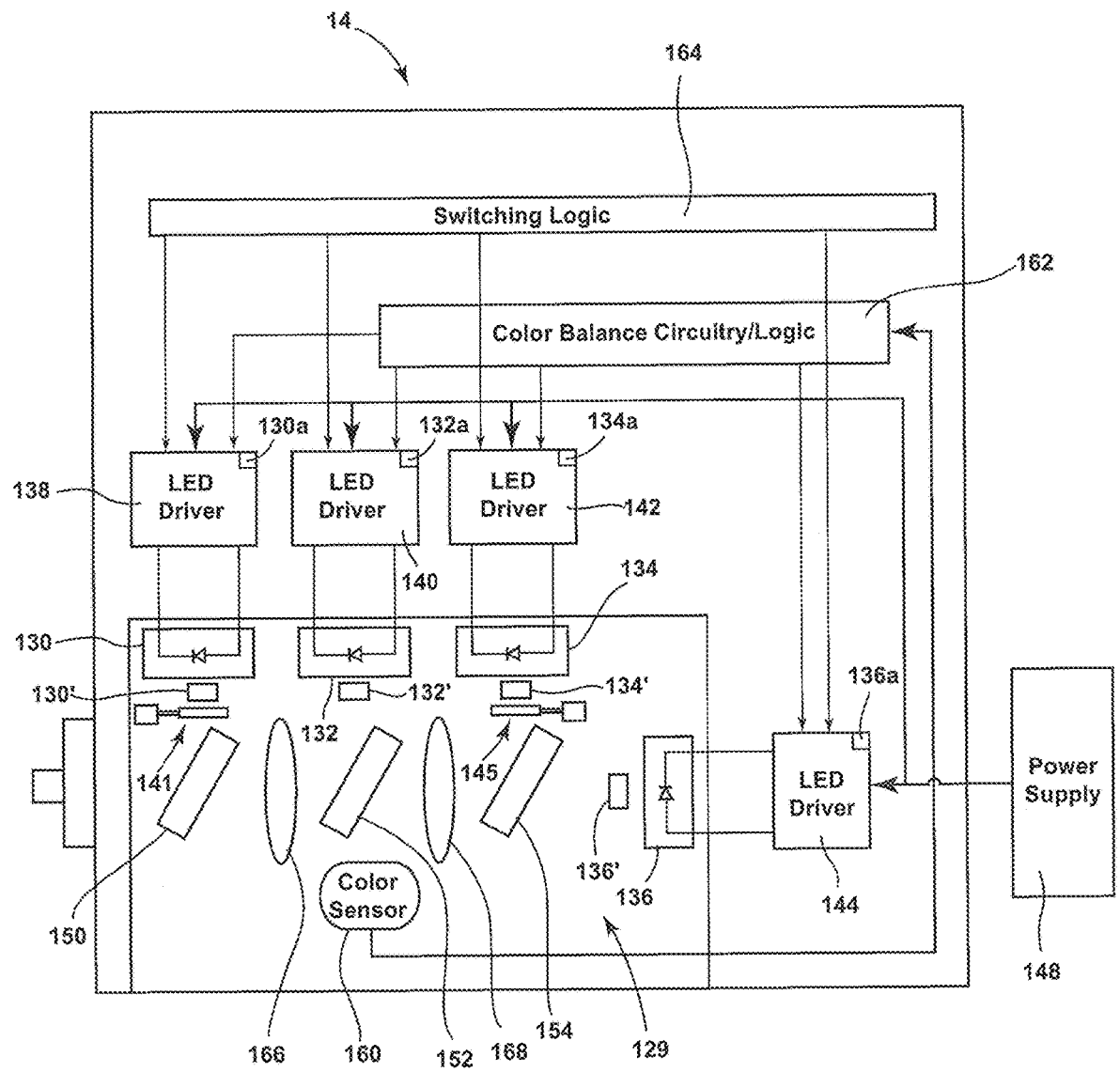
FIG. 4 is a block diagram of a light source of the endoscopic system of FIG. 1.

The light source 14 depicted in FIG. 4 may generate light in five modes: (1) white light (a combination of red, green, and blue light), (2) a limited band imaging mode using the UV LED with a 415-nm filter and the green LED with a 540-nm filter, (3) a UV fluorescent mode using only the UV LED (and preferably no filter), which includes, but is not limited to, a 5-ALA fluorescence mode, (4) a fluorescein mode using the UV LED and the blue LED, preferably without filters, and (5) an endoscope defogging mode in which all of the UV LED, the blue LED, the green LED, and the red LED are used.

In all five modes, the light is transmitted to and through an optic lens output system 22 (see FIG. 2) which focuses light onto a light pipe 24. The light pipe 24 preferably has a diameter substantially similar to the diameter of the fiber bundle of the endoscope and creates a homogeneous light, which is then transmitted to the fiber optic light guide 26. The light guide 26 includes multiple optic fibers and is connected to a light post 28, which is part of the endoscope 12. As described above, the endoscope 12 has an illumination pathway and an optical channel pathway.

The endoscope 12 may include a notch filter 8, which allows at least 80% of infrared light in a wavelength range of 830 nm to 870 nm to pass therethrough and allows at least 80% of visible light in the wavelength range of 400 nm to 700 nm to pass therethrough, but blocks light having a wavelength of 808 nm, and other similar wavelengths, if desired or more practical. The notch filter 8 should have an optical density of OD5 or higher. Alternatively, the notch filter 8 can be located in the coupler 13.

The basic components of the light source 14 are shown in FIG. 4. The light source 14 includes an LED and filter section 129, which has a first LED 130, a second LED 132, a third LED 134, and a fourth LED 136. Preferably, the first LED 130 emits light in the ultraviolet spectrum (preferably 400-440 nm and more preferably 405-420 nm) and includes light having a wavelength range of 407-409 nm, the second LED 132 emits light in the blue wavelength spectrum, the third LED 134 emits light in the green wavelength spectrum, and the fourth LED 136 emits light in the red wavelength spectrum. The first LED 130 is activated by a first LED driver 138, the second LED 132 is activated by a second LED driver 140, the third LED 134 is activated by a third LED driver 142, and the fourth LED 136 is activated by a fourth LED driver 144. The drivers 138, 140, 142, 144 are each powered by an external power supply 148.

The electrical currents supplied to the LEDs 130, 132, 134, 136, are adjusted using a Digital-to-Analog Converter (DAC) 130a for the UV LED 130, a DAC 132a for the blue LED 132, a DAC 134a for the green LED 134, and a DAC 136a for the red LED 136.

Adjacent the first LED 130 is a first optical component 130', adjacent the second LED 132 is a second optical component 132', adjacent the third LED 134 is a third optical component 134', and adjacent the fourth LED 136 is a fourth optical component 136'. The optical components 130', 132', 134', 136' are for the purpose of decreasing the angles of the paths of the light emitted from the LEDs 130, 132, 134, 136, respectively. The optical components 130', 132', 134', 136' may be any component that is capable of achieving the desired purpose, but preferably are lenses or light pipes.

Adjacent the first optical component 130' is a first motorized movable filter 141, and adjacent the third optical component 134' is a second motorized movable filter 145. The movable filters 141, 145 may be used to filter light from the first and third LEDs 130, 134, respectively, or not used depending on the desired imaging mode, as discussed below.

The first motorized movable filter 141 includes an optical filter 141' and a motor 141" (see FIGS. 5-9). Activation of the motor 141" allows the optical filter 141' to be moved into or out of the pathway along which light emitted by the first LED 130 travels. The second motorized movable filter 145 includes an optical filter 145' and a motor 145". Activation of the motor 145" allows the optical filter 145' to be moved into or out of the pathway along which light emitted by the third LED 134 travels.

Adjacent the first movable filter 141 is a first dichroic filter 150, adjacent the second optical component 132' is a second dichroic filter 152, and adjacent both the second movable filter 145 and the fourth optical component 136' is a third dichroic filter 154. The dichroic filters 150, 152, 154 are each designed to reflect certain light and allow passage of other light therethrough, as described in more detail below.

A color sensor 160 is positioned adjacent the second dichroic filter 152, at a location opposite the second LED 132. The color sensor 160 detects light in the visible light wavelength spectrum, and when visible light is detected, it provides a signal to a color balance circuit/logic device 162. The amount of visible light detected is used by the color balance circuit/logic device 162 to provide signals to the LED drivers 140, 142, 144 to adjust the intensity of one or more of the LEDs 132, 134, 136, such that the preferred balance of light in the visible spectrum is achieved. A switching logic device 164 is provided which switches the light source 14 among the various modes of the light source 14.

FIGS. 5-9 show a more detailed view of the LED and filter section 129 of the first embodiment. In this arrangement, the first dichroic filter 150 allows all visible light (i.e. light in the blue, green, and red wavelength spectra) to pass, while reflecting ultraviolet light. The second dichroic filter 152 allows light in the red and green wavelength spectra to pass while reflecting light in the blue wavelength spectrum. The third dichroic filter 154 allows light in the red wavelength spectrum to pass, while reflecting light in the green wavelength spectrum. A first optical lens 166 is located between the first dichroic filter 150 and the second dichroic filter 152, and is for focusing light received from the second dichroic filter 152 to be passed to the first dichroic filter 150. A second optical lens 168 is located between the second dichroic filter 152 and the third dichroic filter 154, and is for focusing light received from the third dichroic filter 154 to be passed to the second dichroic filter 152.

Figure 5:
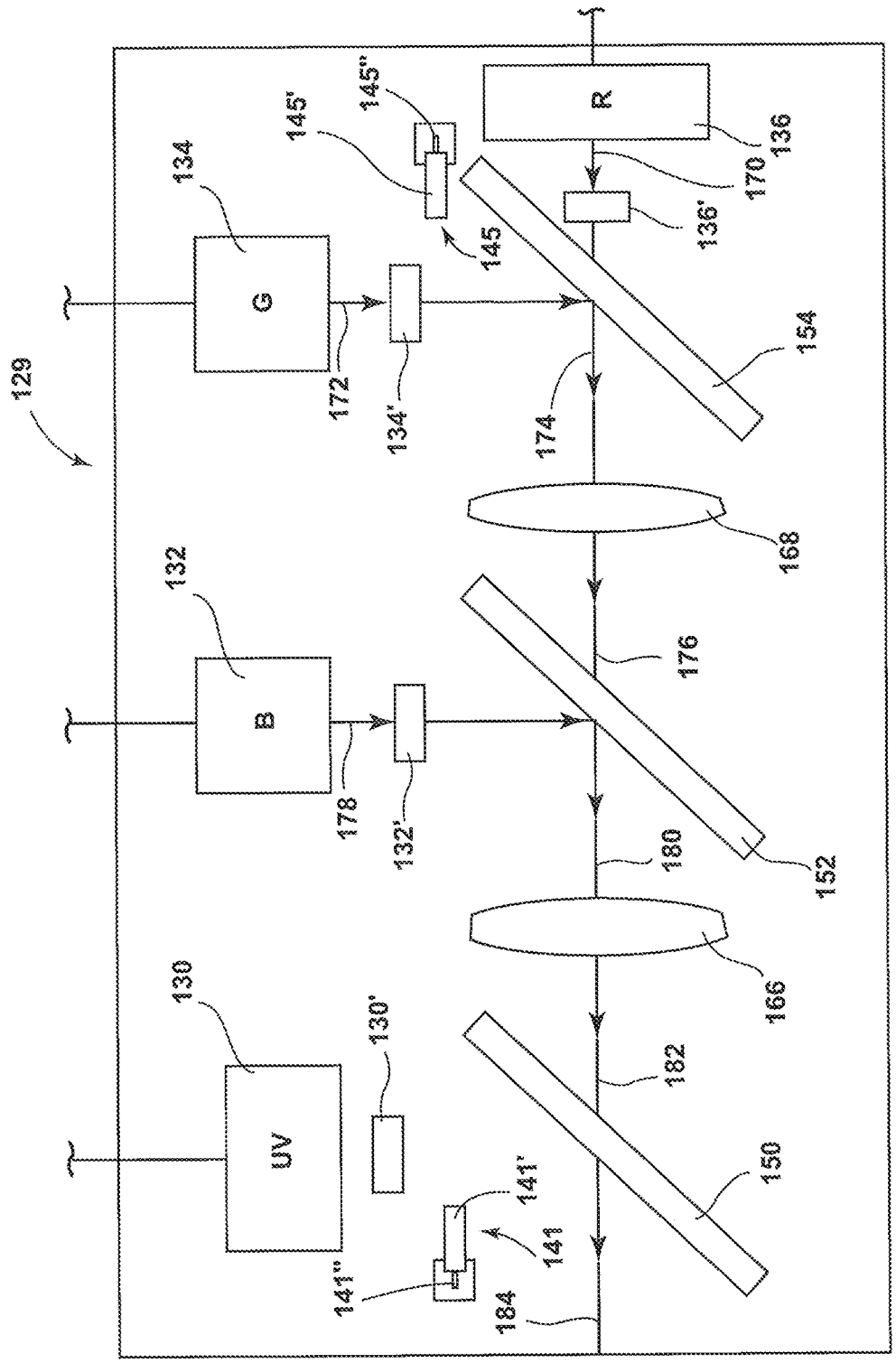
FIG. 5 is a diagrammatic view of the light and filter portion of the light source of FIG. 4 with movable filters out of the light paths, and showing a light emission first mode.

In operation in the first mode, shown in FIG. 5, power is not supplied to the first LED driver 138, but is supplied to the second LED driver 140, the third LED driver 142, and the fourth LED driver 144. Thus, in this mode, no light is provided by the first LED 130, but light is provided by the second LED 132, the third LED 134, and the fourth LED 136. Also, the movable filters 141', 145' are positioned outside of the light paths. Light in the red wavelength spectrum is emitted from the fourth LED 136 in the direction of the pathway 170 toward the fourth optical component 136' and the third dichroic filter 154, as shown in FIG. 5. Light in the green wavelength spectrum is emitted from the third LED 134 in the direction of the pathway 172 toward the third optical component 134' and the third dichroic filter 154. Because the third dichroic filter 154 allows red light to pass and reflects green light, the light along the pathway 174 is a mixture of light in the red and green wavelength spectra. This mixture of light from the pathway 174 is focused by the second optical lens 168 and transmitted along the pathway 176 to the second dichroic filter 152. Light in the blue wavelength spectrum is emitted by the second LED 132 along the pathway 178 toward the second optical component 132' and the second dichroic filter 152. Because the second dichroic filter 152 allows red and green light to pass and reflects blue light, the light along the pathway 180 is a mixture of blue, green, and red light. This light is transmitted along the pathway 180 and through optical lens 166, which focuses the light. The focused blue, green, and red light mixture is transmitted along the pathway 182 toward the first dichroic filter 150, which allows blue light, green light, and red light to pass. Thus, all of the light transmitted along the pathway 182 passes through the first dichroic filter 150 to an exit pathway 184. The mixture of blue light, green light, and red light, i.e. white light, is transmitted along the exit pathway 184 to the lens system 22, as shown in FIG. 2.

Figure 6:
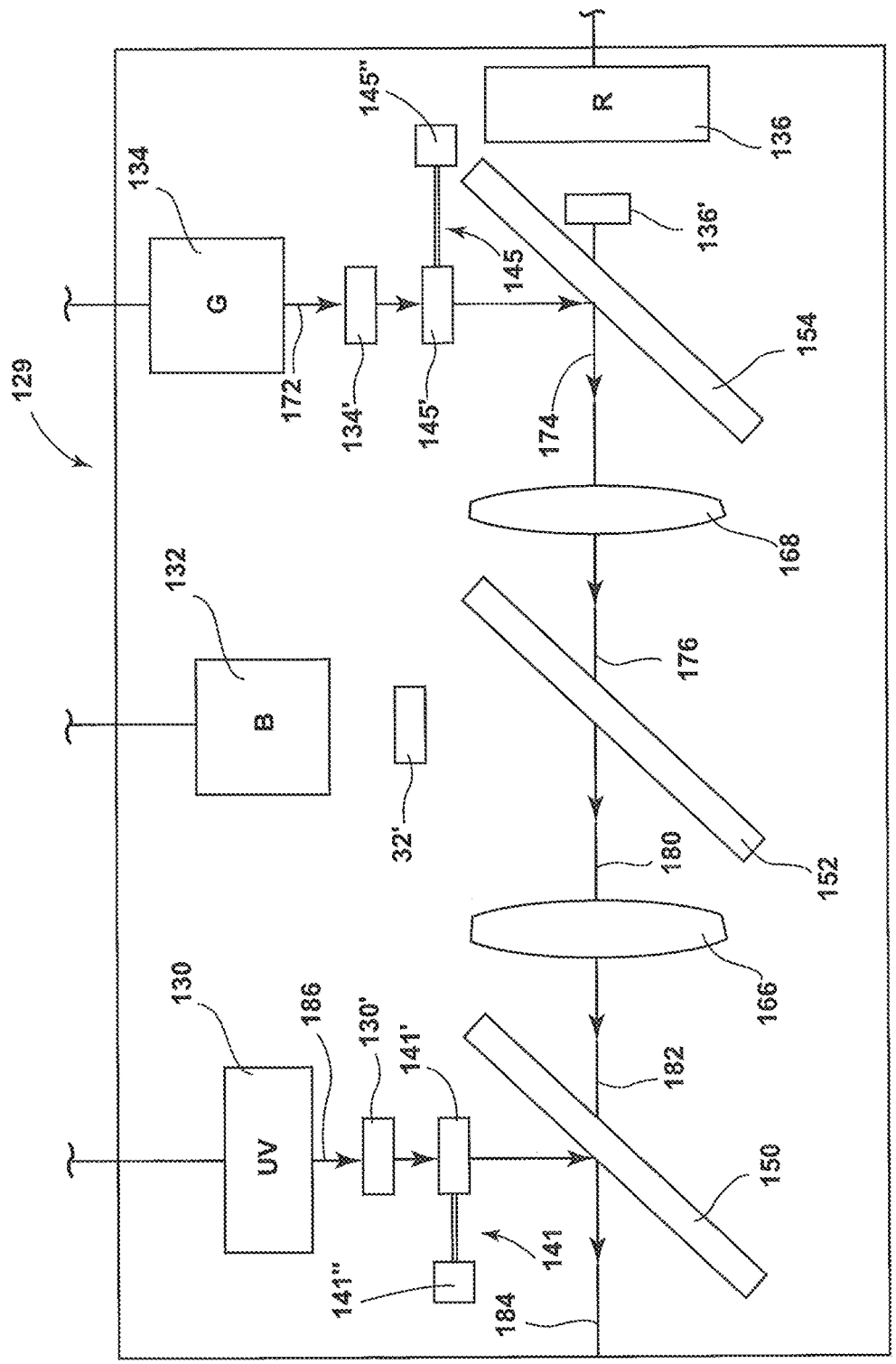
FIG. 6 is a diagrammatic view of the LED and filter portion of FIG. 5 with movable filters in the light paths of an ultraviolet light and a green light, and showing a light emission second mode.

In the second mode, shown in FIG. 6, power is provided to the first LED driver 138 and to the third LED driver 142, but is not provided to the second LED driver 140 or the fourth LED driver 144. Thus, the light source 14 provides ultraviolet light and light in the green wavelength spectrum. Because the second LED 132 and the fourth LED 136 provide no light in this mode, there is no light transmitted along the pathways 178 and 170 (see FIG. 5). In this mode, the movable filters 141', 145' are positioned in the pathways 186, 172, respectively, for filtering of the light emissions of the first LED 130 and the third LED 134. The third LED 134 emits light in the green wavelength spectrum along pathway 172 in the direction of the third optical component 134', the movable filter 145', and the third dichroic filter 154, which reflects the green light. The movable filter 145' filters the light from the LED 134 such that light reaching the dichroic filter 154 along pathway 172 is only visible light having a wavelength of approximately 540 nm. As a result, the 540-nm light is transmitted along the pathway 174, to and through the optical lens 168, along the pathway 176 to the second dichroic filter 152, along the pathway 180 to and through the lens 166, and along pathway 182 to the dichroic filter 150. The first LED 130 emits ultraviolet light along the pathway 186 in the direction of the first optical component 130', the movable filter 141', and the first dichroic filter 150. The light reaching the movable filter 141' is filtered such that light reaching the dichroic filter 150 along pathway 186 is only ultraviolet light having a wavelength of approximately 415 nm. Because the first dichroic filter 150 passes light in the visible wavelength spectrum, and reflects ultraviolet light, the result of light transmitted along the exit pathway 184 is a mixture of 540-nm visible light, and 415-nm ultraviolet light, as shown in FIG. 6. This mixture of light is transmitted to the lens system 22.

Figure 7:
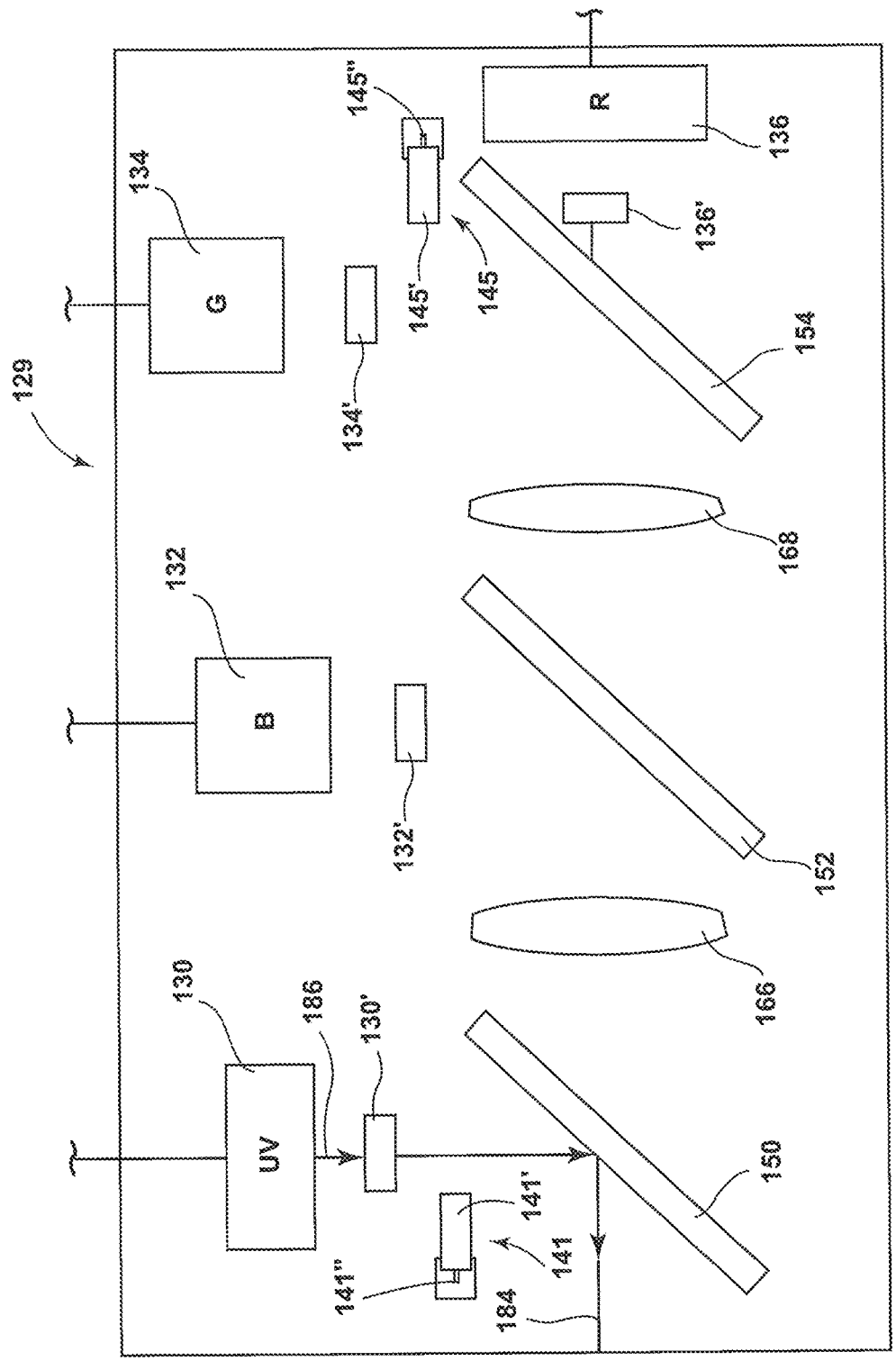
FIG. 7 is a diagrammatic view of the LED and filter portion of FIG. 5, and showing a light emission third mode.

As shown in FIG. 7, operation in the third mode involves supplying power to only the first LED 130. Power is not supplied to the second LED 132, the third LED 134, or the fourth LED 136. The movable filter 141' is positioned outside of the light pathway 186 such that light from the first LED 130 travels along pathway 186 to and through the optical component 130', and to the dichroic filter 150. The UV light emitted by the first LED 130 is reflected by the first dichroic filter 150, and thus the light from the first LED 130 moves along the exit pathway 184 to the lens system 22.

Figure 8:
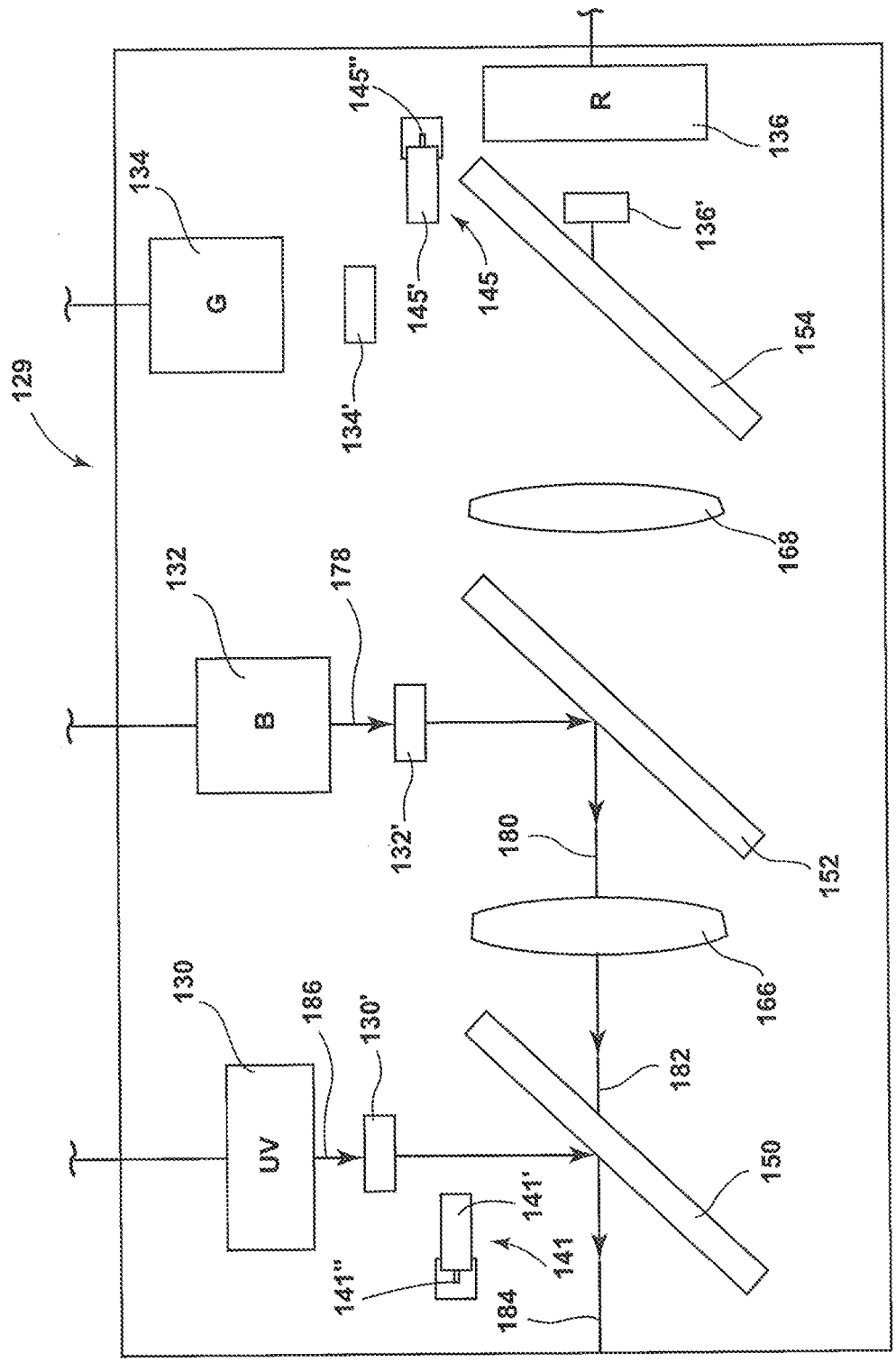
FIG. 8 is a diagrammatic view of the LED and filter portion of FIG. 5, and showing a light emission fourth mode.

In the fourth mode, shown in FIG. 8, power is supplied to the first LED driver 138 and the second LED driver 140, but is not supplied to the third LED driver 142 and the fourth LED driver 144. Thus, in this mode, light is provided only by the first LED 130 and the second LED 132. Also, the movable filters 141', 145' are positioned outside of the light paths. Light in the blue wavelength spectrum is emitted by the second LED 132 along the pathway 178 toward the second optical component 132' and the second dichroic filter 152. This light is reflected by the second dichroic filter 152 and transmitted along the pathway 180 and through optical lens 166, which focuses the light. The focused blue light is transmitted along the pathway 182 toward the first dichroic filter 150, which allows blue light to pass. Light in the UV wavelength spectrum is emitted from the first LED 130 in the direction of pathway 186 toward the first optical component 130', and to the dichroic filter 150. The UV light emitted by the first LED 130 is reflected by the first dichroic filter 150. The mixture of UV and blue light is transmitted along the exit pathway 184 to the lens system 22, as shown in FIG. 2.

Figure 9:
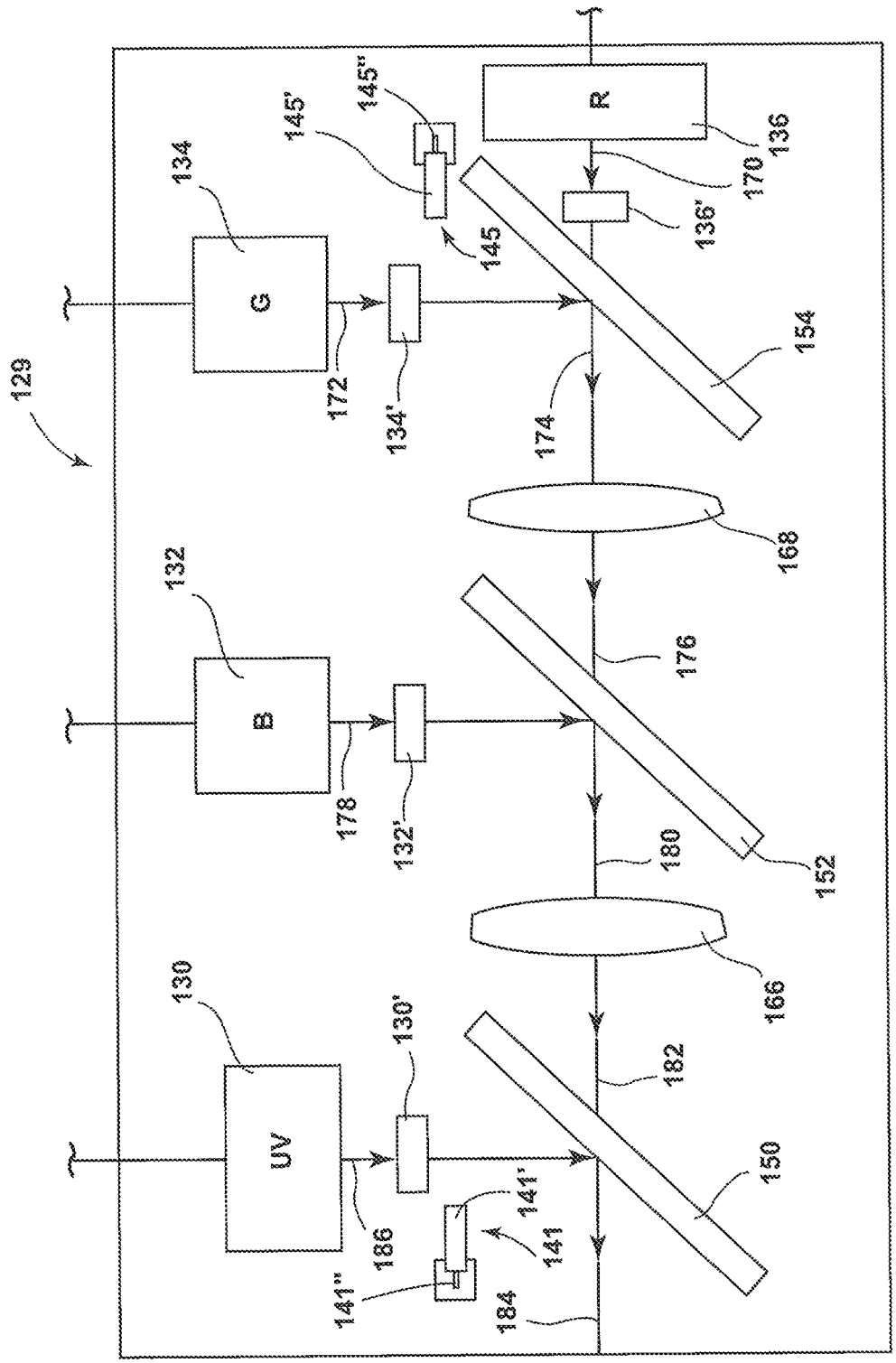
FIG. 9 is a diagrammatic view of the LED and filter portion of FIG. 5, and showing a light emission fifth mode.

In the fifth mode, shown in FIG. 9, power is supplied to the first LED driver 138, the second LED driver 140, the third LED driver 142, and the fourth LED driver 144. Thus, in this mode, light is provided by the first LED 130, the second LED 132, the third LED 134, and the fourth LED 136. Also, the movable filters 141', 145' are positioned outside of the light paths. Light in the red wavelength spectrum is emitted from the fourth LED 136 in the direction of the pathway 170 toward the fourth optical component 136' and the third dichroic filter 154, as shown in FIG. 9. Light in the green wavelength spectrum is emitted from the third LED 134 in the direction of the pathway 172 toward the third optical component 134' and the third dichroic filter 154. Because the third dichroic filter 154 allows red light to pass and reflects green light, the light along the pathway 174 is a mixture of light in the red and green wavelength spectra. This mixture of light from the pathway 174 is focused by the second optical lens 168 and transmitted along the pathway 176 to the second dichroic filter 152. Light in the blue wavelength spectrum is emitted by the second LED 132 along the pathway 178 toward the second optical component 132' and the second dichroic filter 152. Because the second dichroic filter 152 allows red and green light to pass and reflects blue light, the light along the pathway 180 is a mixture of blue, green, and red light. This light is transmitted along the pathway 180 and through optical lens 166, which focuses the light. The focused blue, green, and red light mixture is transmitted along the pathway 182 toward the first dichroic filter 150, which allows blue light, green light, and red light to pass. Light in the UV wavelength spectrum is emitted from the first LED 130 in the direction of pathway 186 toward the first optical component 130', and to the dichroic filter 150. The UV light emitted by the first LED 130 is reflected by the first dichroic filter 150. The mixture of UV light, blue light, green light, and red light is transmitted along the exit pathway 184 to the lens system 22, as shown in FIG. 2.

After the light, in the first mode, the second mode, the third mode, fourth mode, or fifth mode passes through the lens system 22, it is transmitted through the light pipe 24, through the fiber optic light guide 26, and to the endoscope 12 via the light post 28. The light transmits through the illumination pathway of the endoscope to the object 1.

In the first mode, visible light is reflected off of the object 1, a portion of which is received by the endoscope 12, and which is transmitted to the camera head 16 via the optical channel pathway. In the second mode, 415-nm UV light, as well as 540-nm visible light, are transmitted to the object 1. The light is reflected or absorbed by the object 1, and a portion of the reflected light is received by the endoscope 12. In the third mode, UV light is transmitted to the object 1, and excites the fluorescent markers 2 in the object. The excitation of the fluorescent markers 2 causes the markers 2 to emit their own light, which is approximately 633-nm red/pink light. This 633-nm light, along with some reflected light, is transmitted to the camera head 16 via the optical channel pathway. A filter may be used in the endoscope 12 to block excitation light so as to prevent excitation light from washing out the fluorescent emission. In the fourth mode, 415-nm UV light, as well as blue visible light, are transmitted to the object 1. The light in the 465 nm to 490 nm range excites fluorescein markers in the object 1. The excitation of the fluorescent markers causes the markers 2 to emit their own light in the 520 nm to 530 nm range. A filter may be used in the endoscope 12 or in the coupler 13 to prevent reflected blue light from washing out the received light emission. In the fifth mode, UV light, blue light, green light, and red light are all transmitted to and through the endoscope 12. The light emitted can be used to defog the endoscope by reducing or eliminating moisture on the exterior surface 56 of the distal window via absorption of radiation from the light.

The light, in the first mode, the second mode, the third mode, or the fourth mode, returns along a path to the camera head 16 as shown and described in WO 2014/152757 which is herby incorporated by reference in its entirety. The camera head 16 may include a trichroic prism or other filters.

The reference numeral 229 (FIG. 10) generally designates another embodiment of the present invention, being a second embodiment of an LED and filter section of a light source. Since the LED and filter section 229 is similar to the previously-described LED and filter section 129, similar parts and light pathways appearing in FIGS. 1-9 are represented by the same corresponding reference number, except for adding 100 to the previous part numeral of those in FIGS. 1-9.

The LED and filter section 229 includes not only the four LEDs described above for the LED and filter section 129, but also includes an infrared laser diode 243. In front of the laser diode 243 is an optical component 243'. Infrared light emitted from the laser diode 243 travels along light pathway 288 through the optical component 243' and to a dichroic filter 250 which reflects infrared light, and passes blue, green, and red light emitted from LEDs 232, 234, and 236. The infrared and/or blue, green, and red light from the dichroic filter 250 travels along light pathway 284 to and through a lens 269, and then along light pathway 290 to another dichroic filter 251. The dichroic filter 251 passes infrared light, as well as blue, green, and red visible light, while reflecting light in the ultraviolet spectrum. Thus, light emitted from the LED 230 in the ultraviolet spectrum travels along light pathway 286, through an optical component 230' (and optionally a movable filter 241') and is reflected by the dichroic filter 251. Any light from the LEDs 230, 232, 234, 236 and/or light from the laser diode 243 then travels along an exit light pathway 292 to the light output and to and through the optical lens output system 22. The LED and filter portion 229 includes two movable filters 241, 245, which may be moved into or out of the light paths 286, 272, respectively, in similar fashion to that described above with respect to the LED and filter section 129. The laser diode 243 is preferably an infrared diode (denoted by the letters IR) which emits light having a wavelength in the range of about 805 nm to about 810 nm, and more preferably having a wavelength of about 808 nm.

Accordingly, the LED and filter section 229 may function in at least six modes, those being the five modes discussed above, as well as an infrared mode for light emission in a wavelength range of about 805 nm to about 810 nm. This mode is especially useful for using ICG markers which reflect a fluorescence. An additional mode may use the IR light for defogging as described in U.S. Pat. Pub. No. 2014/0200406.

An infrared sensor may be positioned adjacent the first dichroic filter 250, at a location opposite the laser diode 243. The infrared sensor detects the presence of infrared light, and when the presence of infrared light is detected, it provides a signal to a laser diode intensity control circuit. The laser diode intensity control circuit is connected to the laser diode driver and controls the intensity of the light emitted from the laser diode 243.

Figure 10:
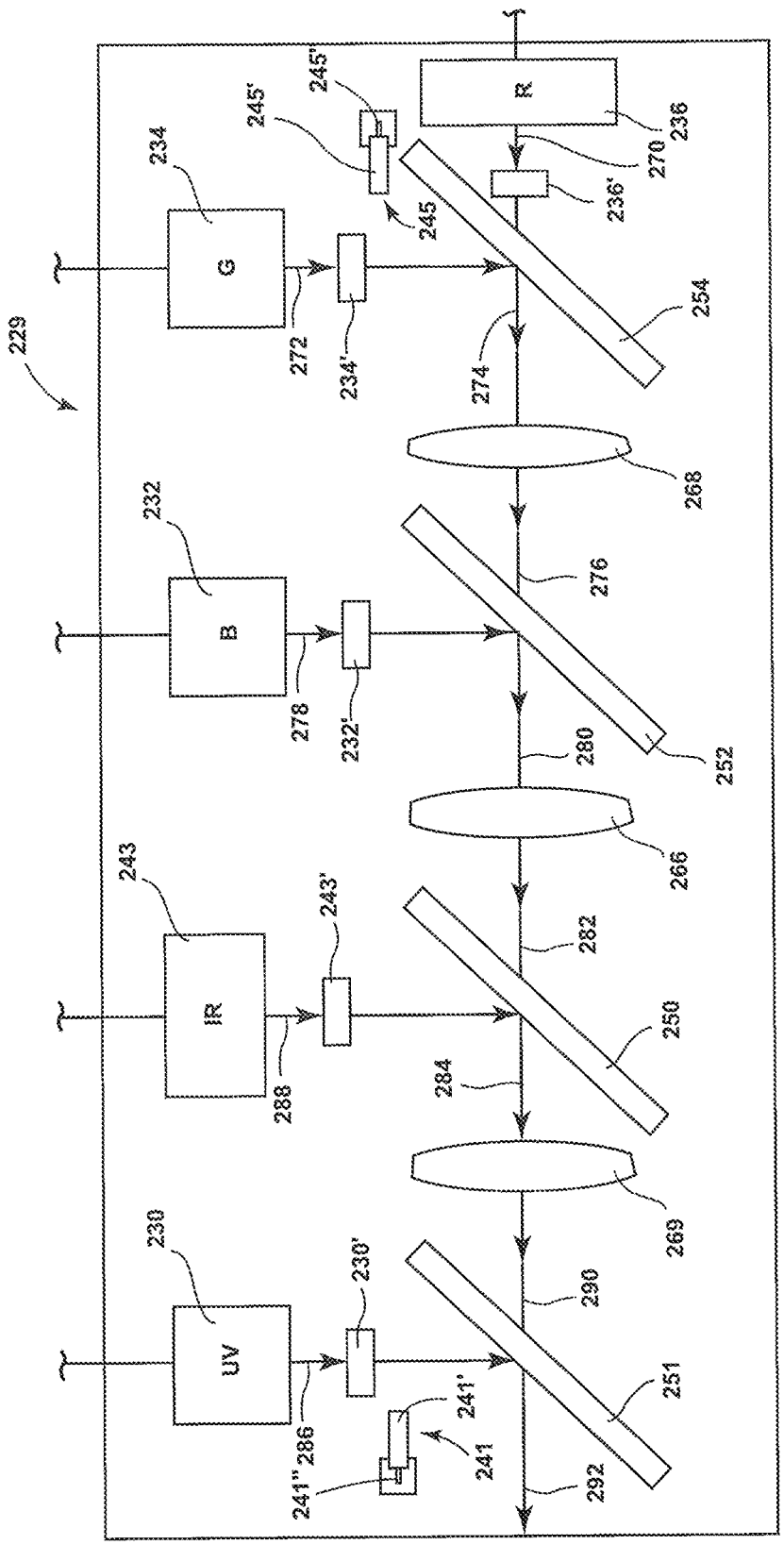
FIG. 10 is a diagrammatic view of a second embodiment of the light and filter portion of the light source of the endoscopic system of FIG. 1, and having LEDs for ultraviolet light, blue light, green light, and red light, and a laser diode for infrared light.
Figure 11:
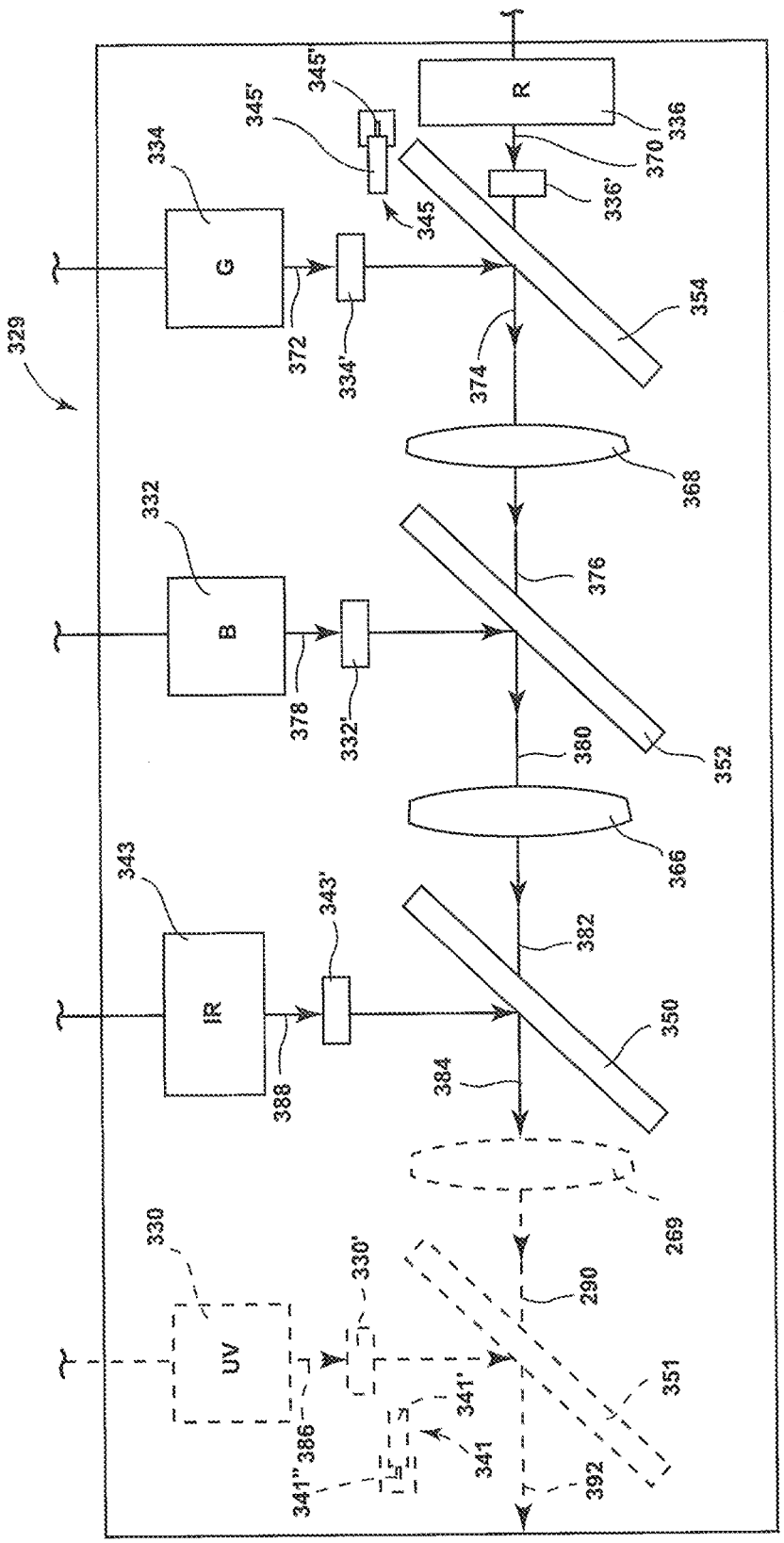
FIG. 11 is a diagrammatic view of a third embodiment of the light and filter portion of the light source of the endoscopic system of FIG. 1, and having LEDs for blue light, green light, and red light, multiple laser diodes for infrared light, and optionally an LED for ultraviolet light.

The reference numeral 329 (FIG. 11) generally designates another embodiment of the present invention, being a third embodiment of an LED and filter section of a light source. Since the LED and filter section 329 is similar to the previously-described LED and filter section 229, similar parts and light pathways appearing in FIG. 10 are represented by the same corresponding reference number, except for adding 100 to the previous part numeral of those in FIG. 10.

The LED and filter section 329 includes a blue LED 332, a green LED 334, a red LED 336, and optionally a UV LED 330. The LED and filter section 329 also includes an infrared laser configuration 343. Due to space constraints in some light source systems, and the desire to have a heat sink available for each LED/laser, the laser configuration 343 includes two infrared laser diodes as shown in FIGS. 12-13.

Figure 12:
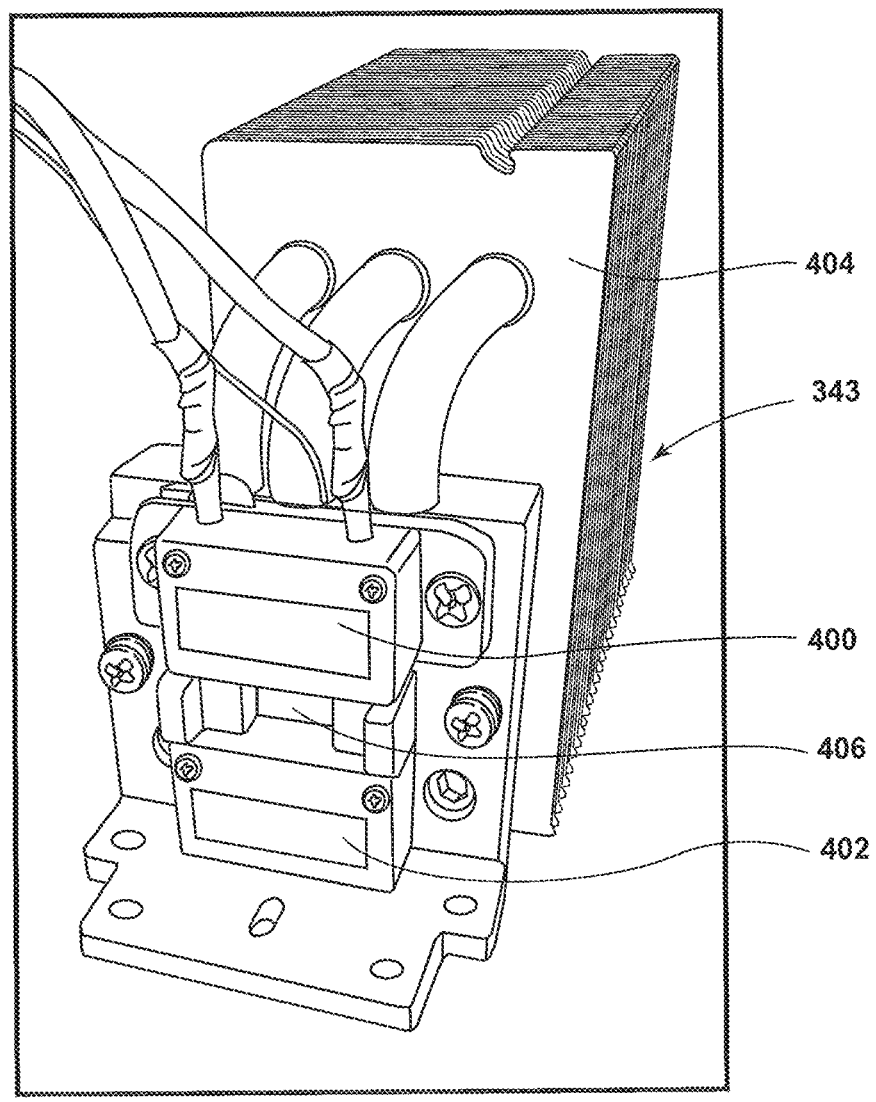
FIG. 12 is a perspective view of a single light source slot in a light engine having two infrared laser diodes, both connected to a single heat sink.

FIG. 12 depicts the infrared laser configuration 343, that includes a first infrared laser diode 400, which preferably emits an 808-nm infrared laser, and a second infrared laser diode 402, which preferably emits a 780-nm infrared laser. Each of the laser diodes 400, 402 are connected to a heat sink 404. The heat sink 404 is capable of absorbing the heat from each of the laser diodes 400, 402, especially since the laser diodes 400, 402 are typically used separately from one another.

Figure 13A:
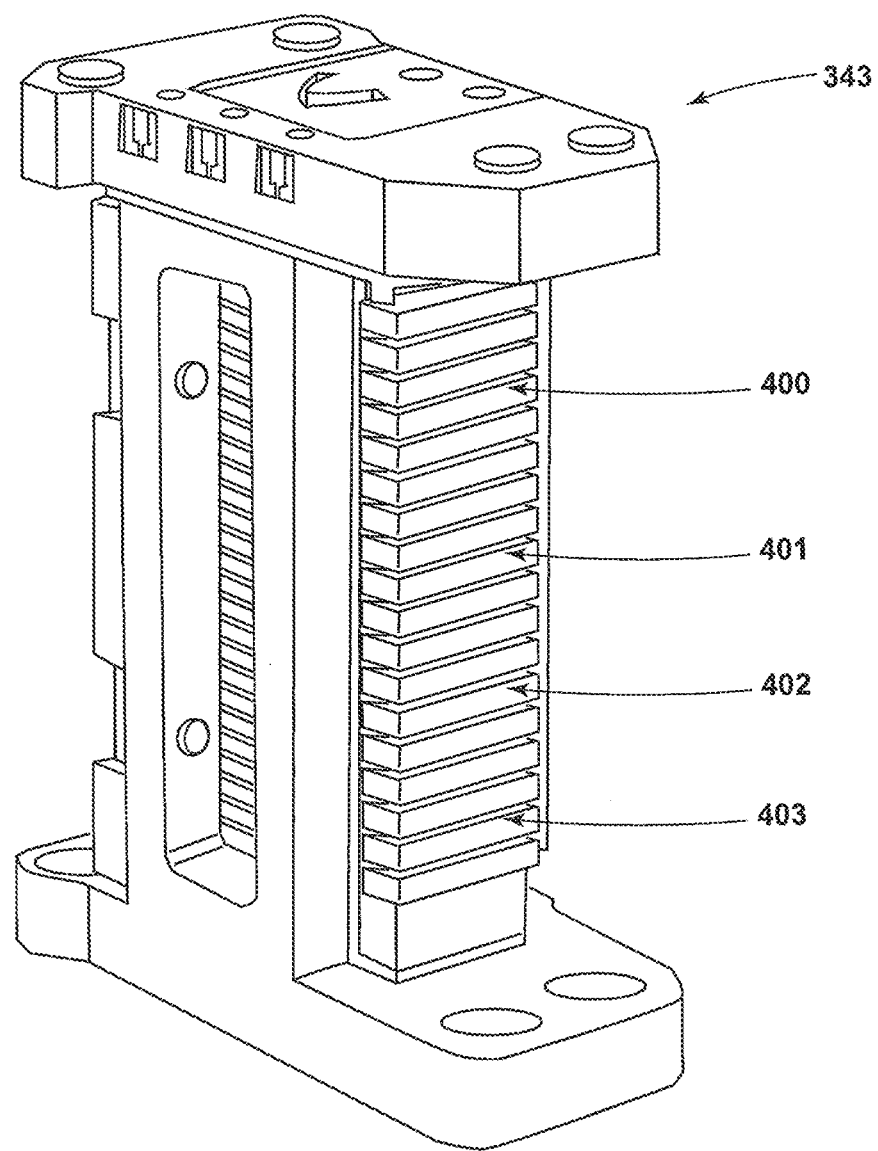
FIG. 13A is a perspective view of a light source stack which includes a plurality of laser diodes.

As shown in FIG. 13A, the laser configuration 343 may include more than two laser diodes. The laser configuration 343 depicted in FIG. 13B has four laser diodes 400, 401, 402, 403, while only using one light source slot/heat sink.

Figure 13B:
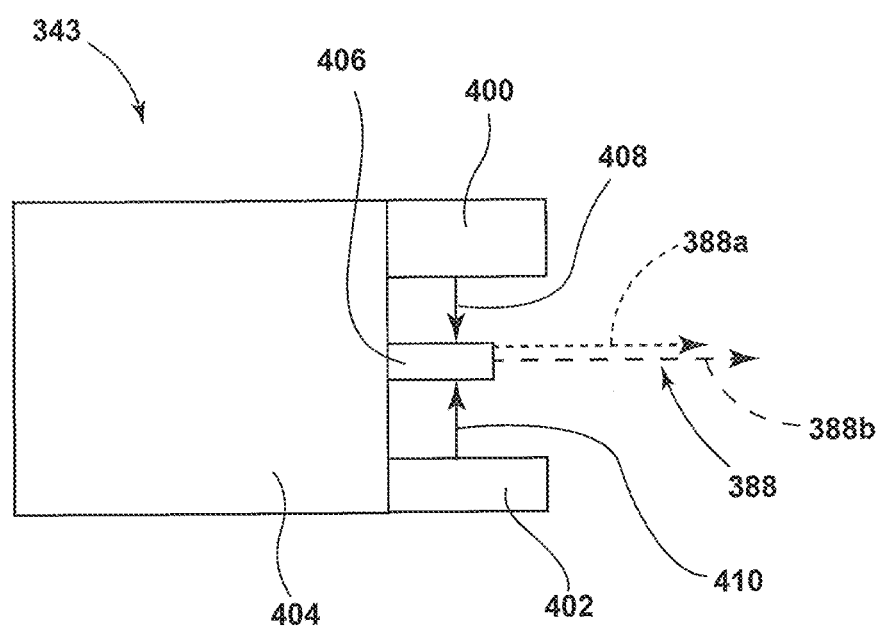
FIG. 13B is an elevational side view of the light source stack, including infrared laser diodes, and a heat sink, of FIG. 12.

In FIGS. 12, 13A, and 13B the laser diodes 400, 401, 402, 403 are shown to be one above the other vertically, however other configurations are contemplated. Preferably though, an optical prism 406 is placed between/among the laser diodes 400, 402 and is capable of receiving an emission from each of the laser diodes, such as laser diodes 400, 402, as shown in FIG. 13B. A laser emission is received by the optical prism 406 from the laser diode 400 via light path 408 and receives a laser emission from laser diode 402 via light path 410. The optical prism 406 is capable of redirecting the emissions from laser diodes 400, 402 along light path 388 toward and through an optical component 343' and to a dichroic filter 350. The emissions from the laser diodes 400, 402 are directed out of the optical prism 406 along concentric optical pathways 388a and 388b, respectively.

Figure 14:
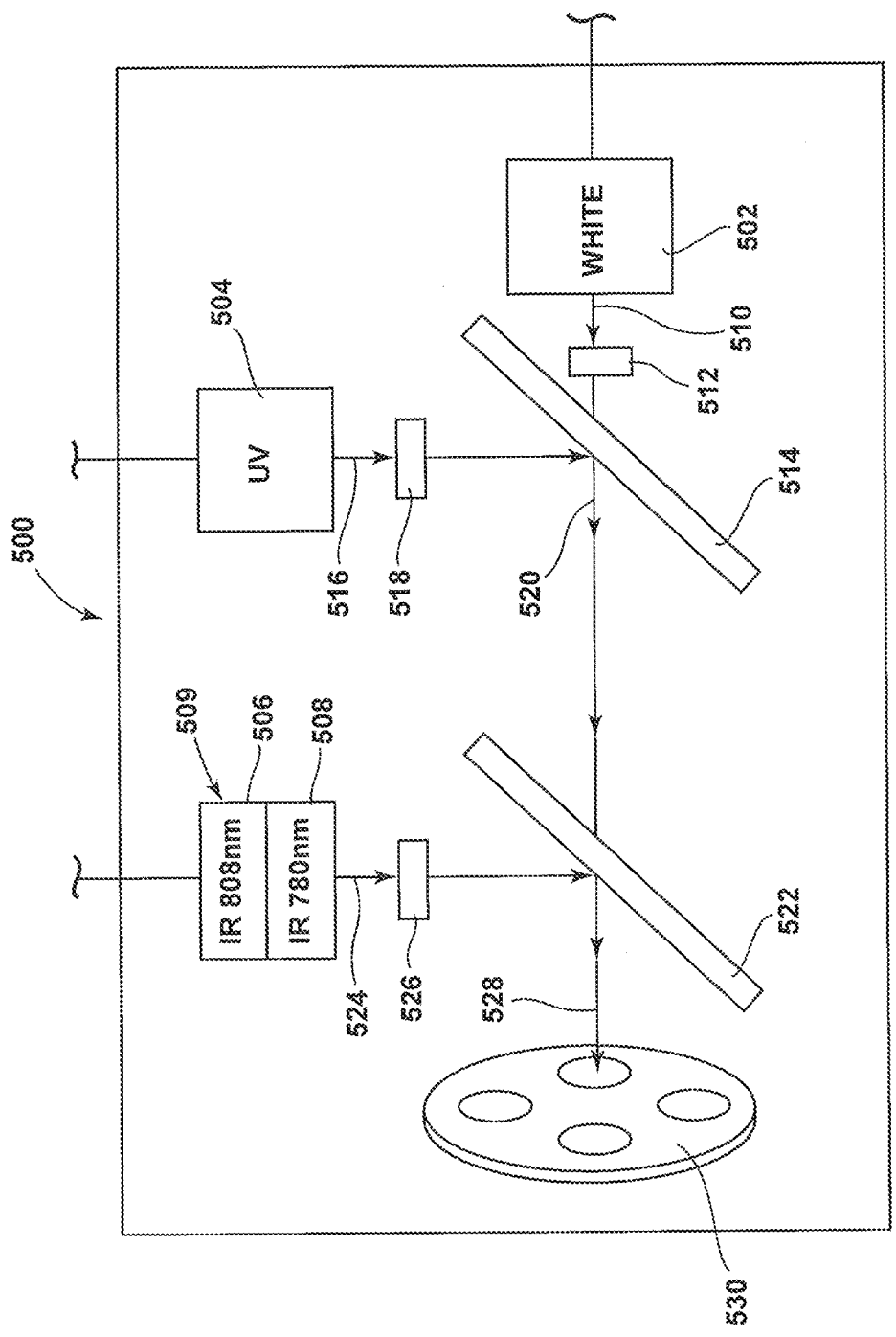
FIG. 14 is a diagrammatic view of a fourth embodiment of the light and filter portion of the light source of the endoscopic system of FIG. 1, and having LEDs for white light and UV light and multiple laser diodes for infrared light.

Another embodiment is depicted in FIG. 14. This embodiment is one that typically would have a small size where space limitations are at a premium. The light source 500 includes four different light emission components. Those light source components are a white light LED 502, a UV LED 504, an infrared 808 nm laser diode 506, and an infrared 780 nm laser diode 508. The infrared 808 nm laser diode 506 and the infrared 780 nm laser diode 508 preferably both use the same "slot" and thus the same heat sink as depicted in FIGS. 12-13.

The white light LED 502 is preferably a powerful LED and can be used during normal endoscopic illumination. The white light emitted from the LED 502 could be filtered and separated into individual color components and used for other imaging modalities. The light emitted from the LED 502 travels along a light path 510 to and through an optical component 512 and to a dichroic filter 514 which allows visible light to pass therethrough.

The LED 504 emits ultraviolet light along a light pathway 516 to and through an optical component 518 and to the dichroic filter 514. The dichroic filter 514 reflects the ultraviolet light from the LED 504 and thus both visible light and ultraviolet light move along light path 520 to a second dichroic filter 522 which allows both visible light and ultraviolet light to pass therethrough.

Infrared light from either laser diode 506 or laser diode 508 is emitted from the slot 509 along a light path 524 to and through an optical component 526 and to the second dichroic filter 522. The second dichroic filter 522 reflects infrared light. Light reflected by or passing through the dichroic filter 522 moves along a light path 528.

The light along light path 528 is directed to a filter mechanism 530, such as a filter wheel, which can change optical filters, depending on the mode desired. It is contemplated that other types of filters could also be used with the light engine 500.

The light engine 500 is capable of multiple imaging modalities, while having a smaller overall footprint size than a typical light engine because it requires fewer heat sinks and slots. The light engine 500 is capable of at least the following imaging modalities: white light, ICG, on target drug (780 nm), UV fluorescent, limited band imaging, fluorescein, and a backlight for laser modes.

Figure 15:
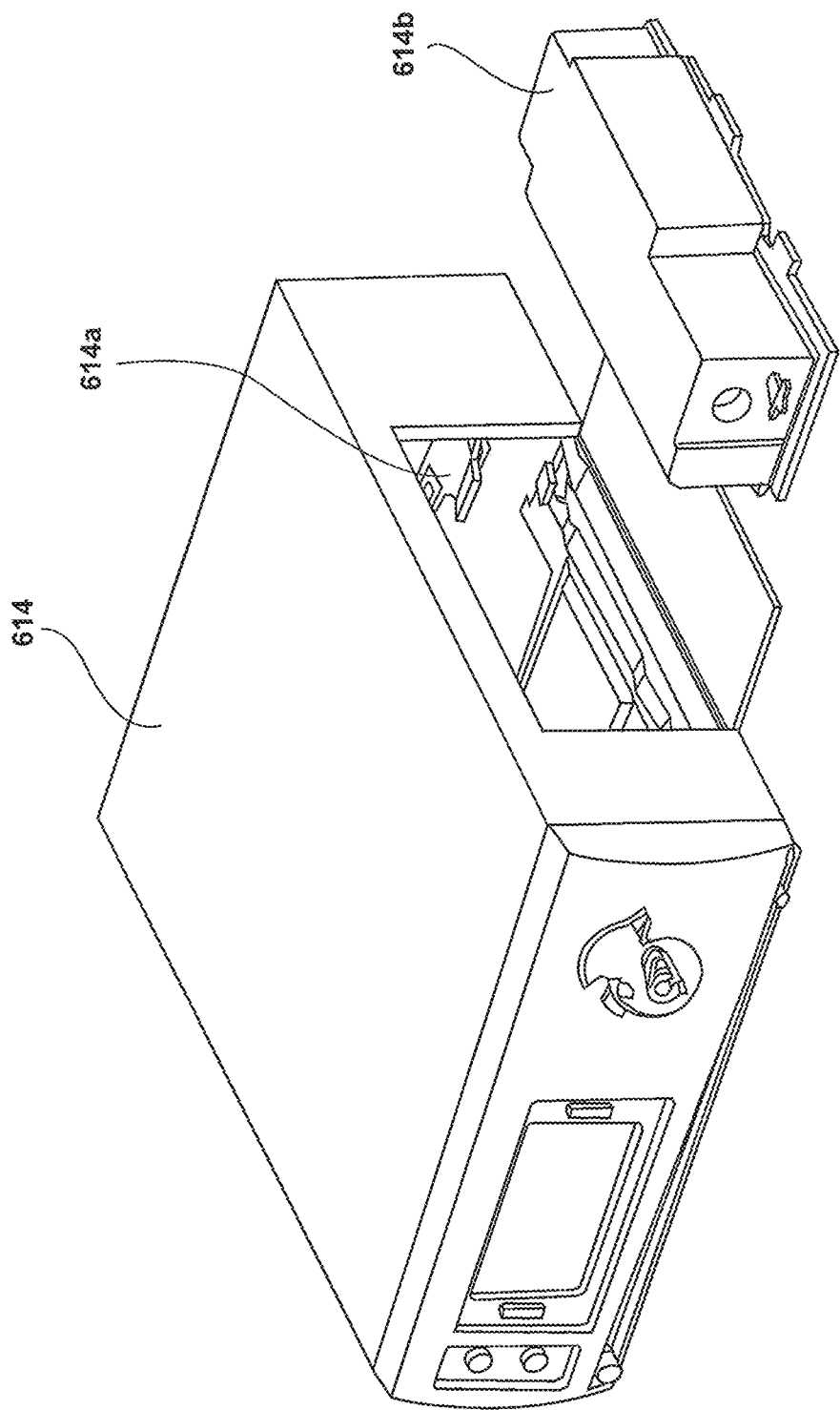
FIG. 15 is a perspective view of a light source with a modular light engine.
Figure 16:
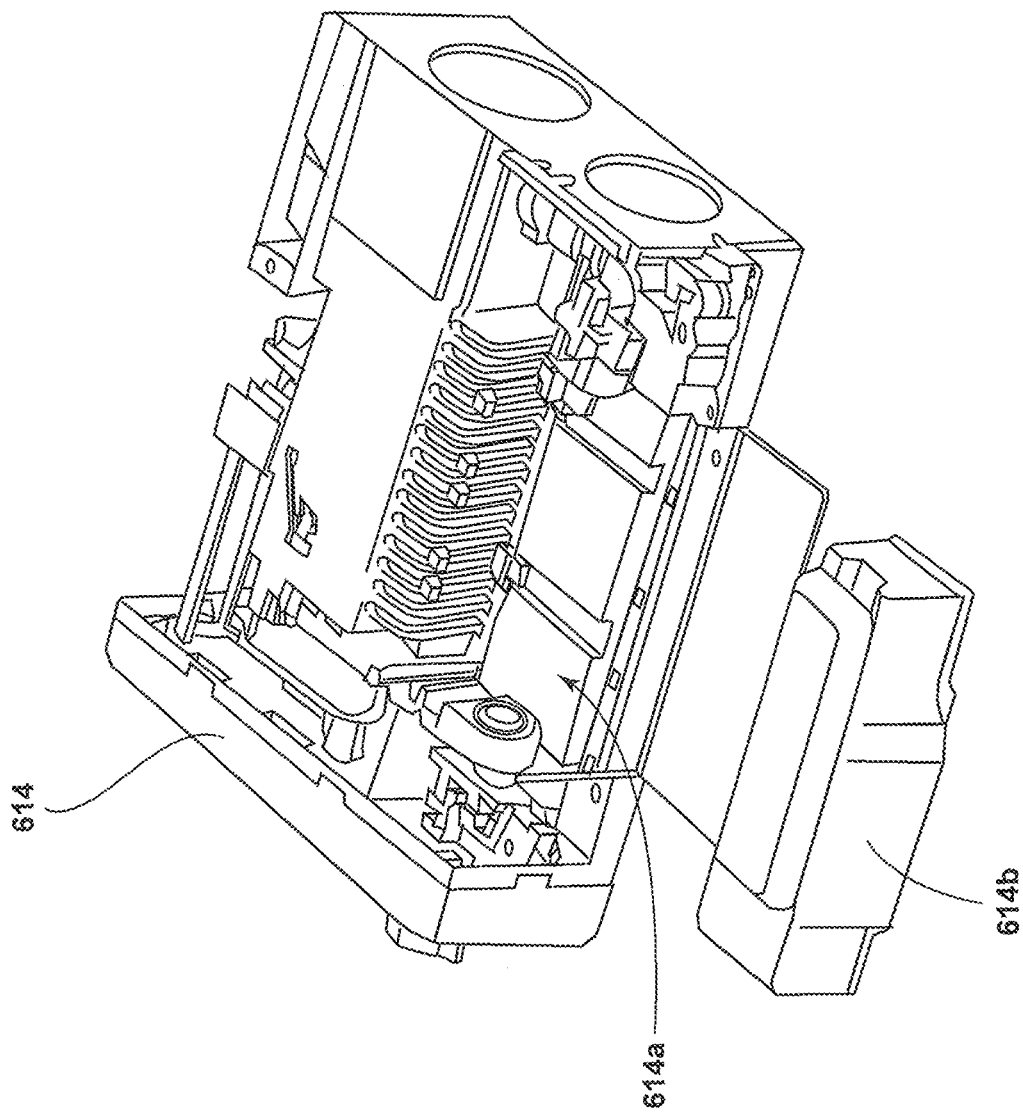
FIG. 16 is a rear perspective view of the light source with modular light engine of FIG. 15, with the housing of the light source removed.
Figure 17:
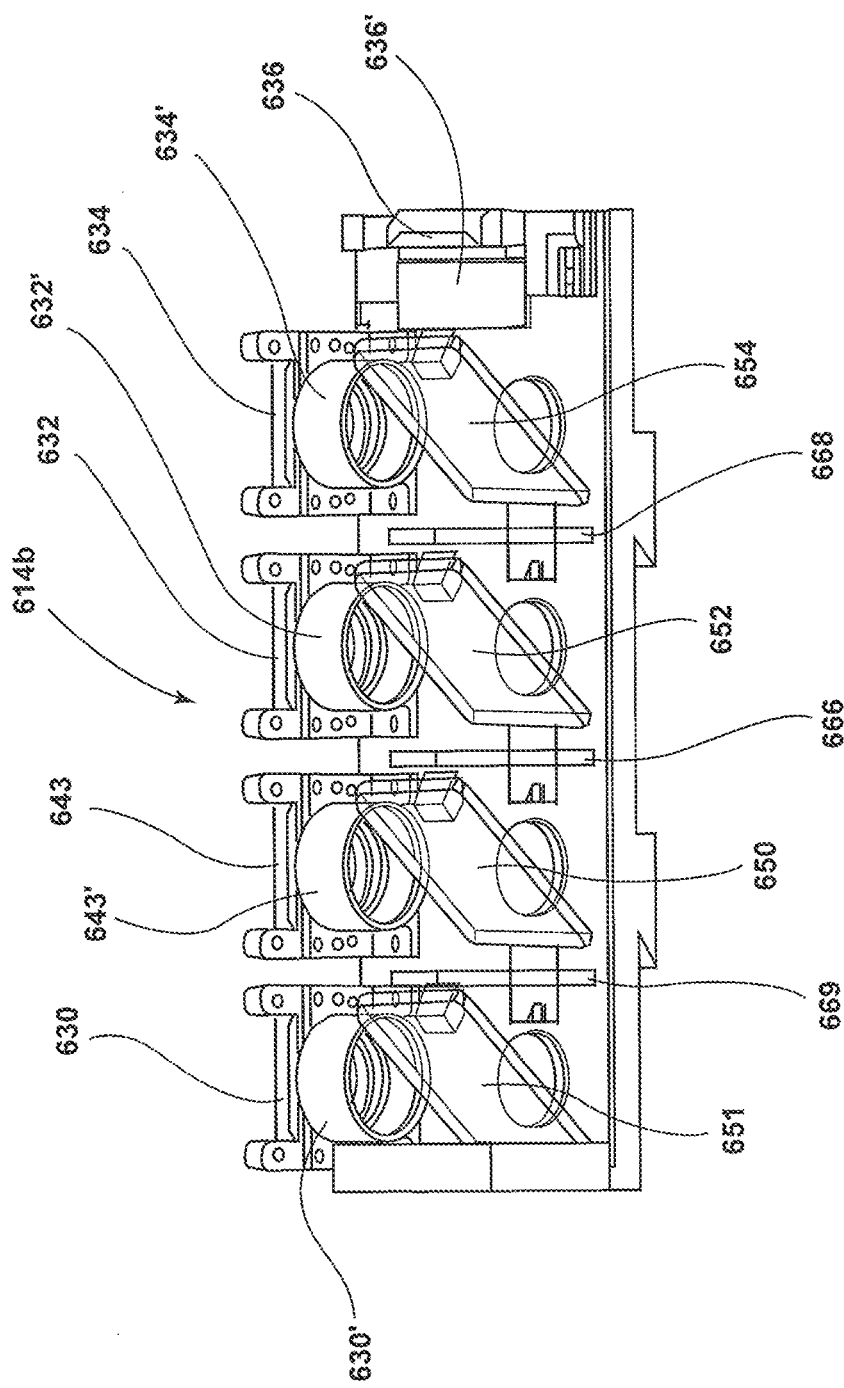
FIG. 17 is a perspective view of the modular light engine of FIG. 15 with the housing removed.

FIGS. 15-17 depict a first embodiment of a modular light engine system for a light source 614. The light source 614 has a port or opening 614a which is shaped and sized to receive a modular light engine 614b. The light source 614 therefore may use interchangeable light engines, such as light engine 614b, which is essentially an LED and filter section similar to that of the LED and filter sections 129, 229, 329, 500 discussed above. Accordingly, the user may select a particular modular light engine for the particular surgical procedure to be performed. Therefore, the modular light engine 614b may include a variety of different filters and lights. An example of such a modular light engine is shown in FIG. 17, which has components similar to the second embodiment of the LED and filter section 229, discussed above. Specifically, the modular light engine 614b depicted in FIG. 17 include LEDs 630, 632, 634, and 636, with corresponding optical components 630', 632', 634', and 636'. In addition, included is a infrared laser diode 643 with corresponding optical component 643'. Four dichroic filters 650, 651, 652, and 654 are included for proper reflection and/or passing of light for a particular mode, and lenses 666, 668, 669 are included for focusing of light.

Figure 18:
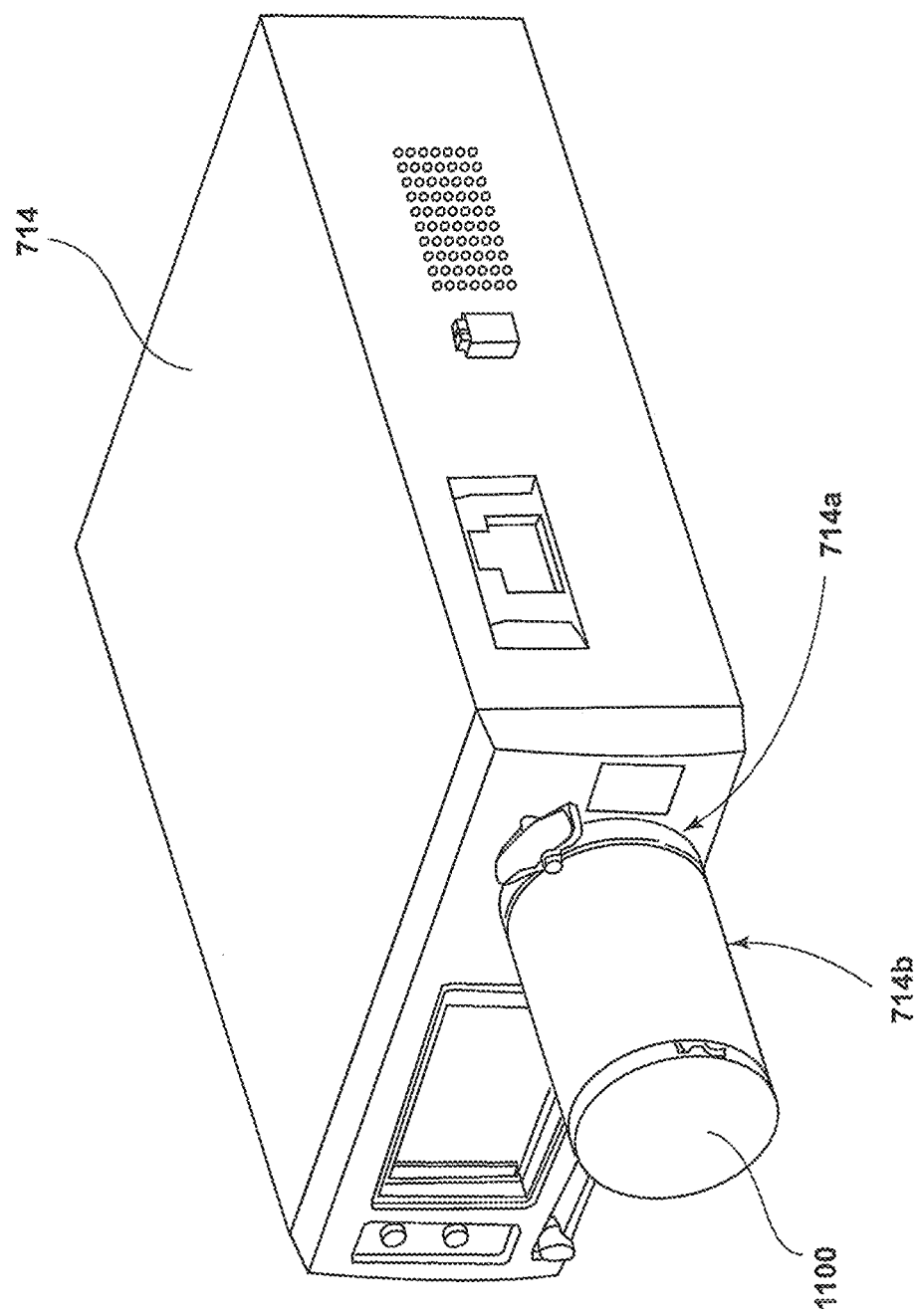
FIG. 18 is a perspective view of a light source with a modular upgrade to the light engine.
Figure 19:
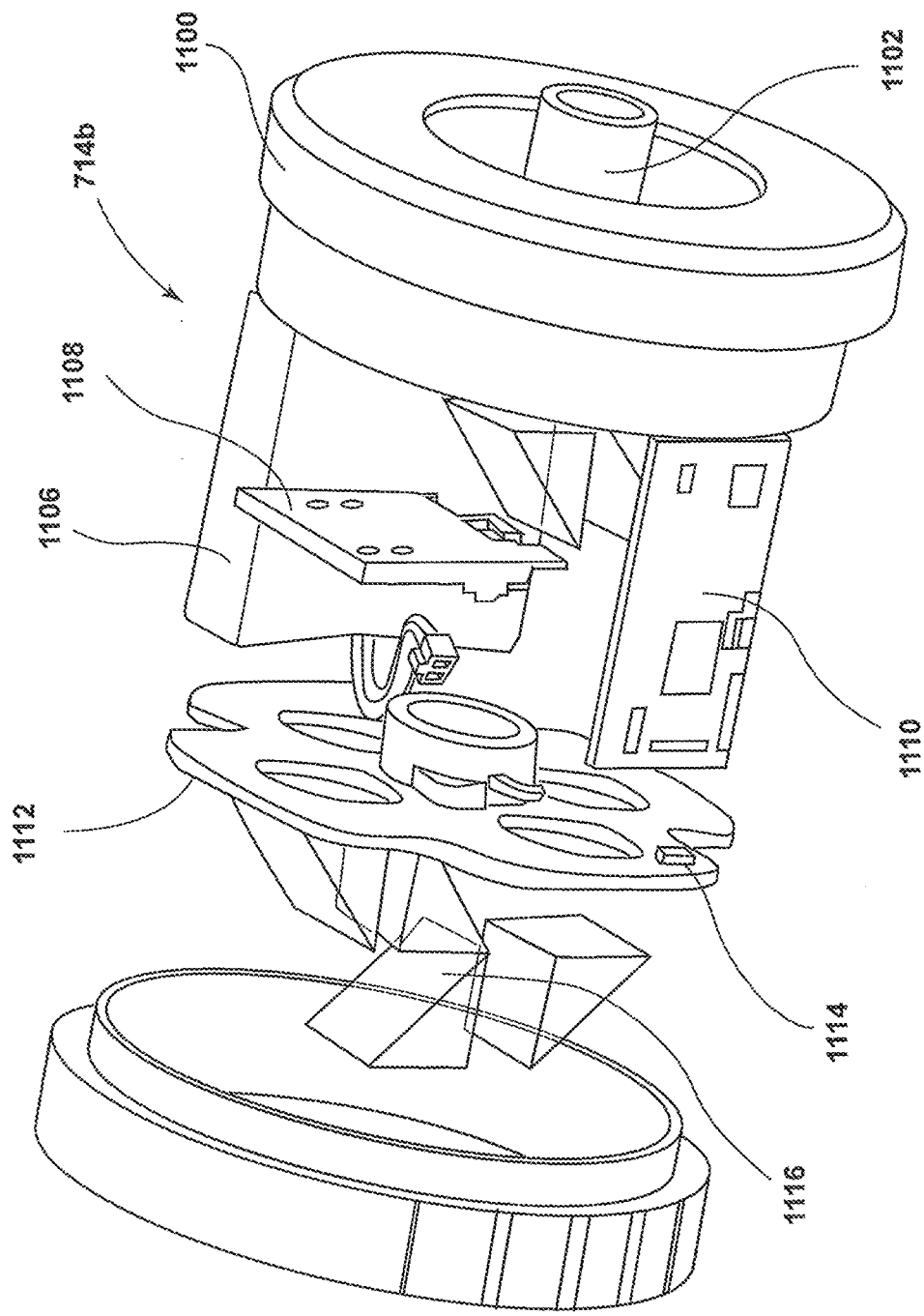
FIG. 19 is a perspective view of the modular upgrade of FIG. 18 with a portion of the housing removed.
Figure 20:
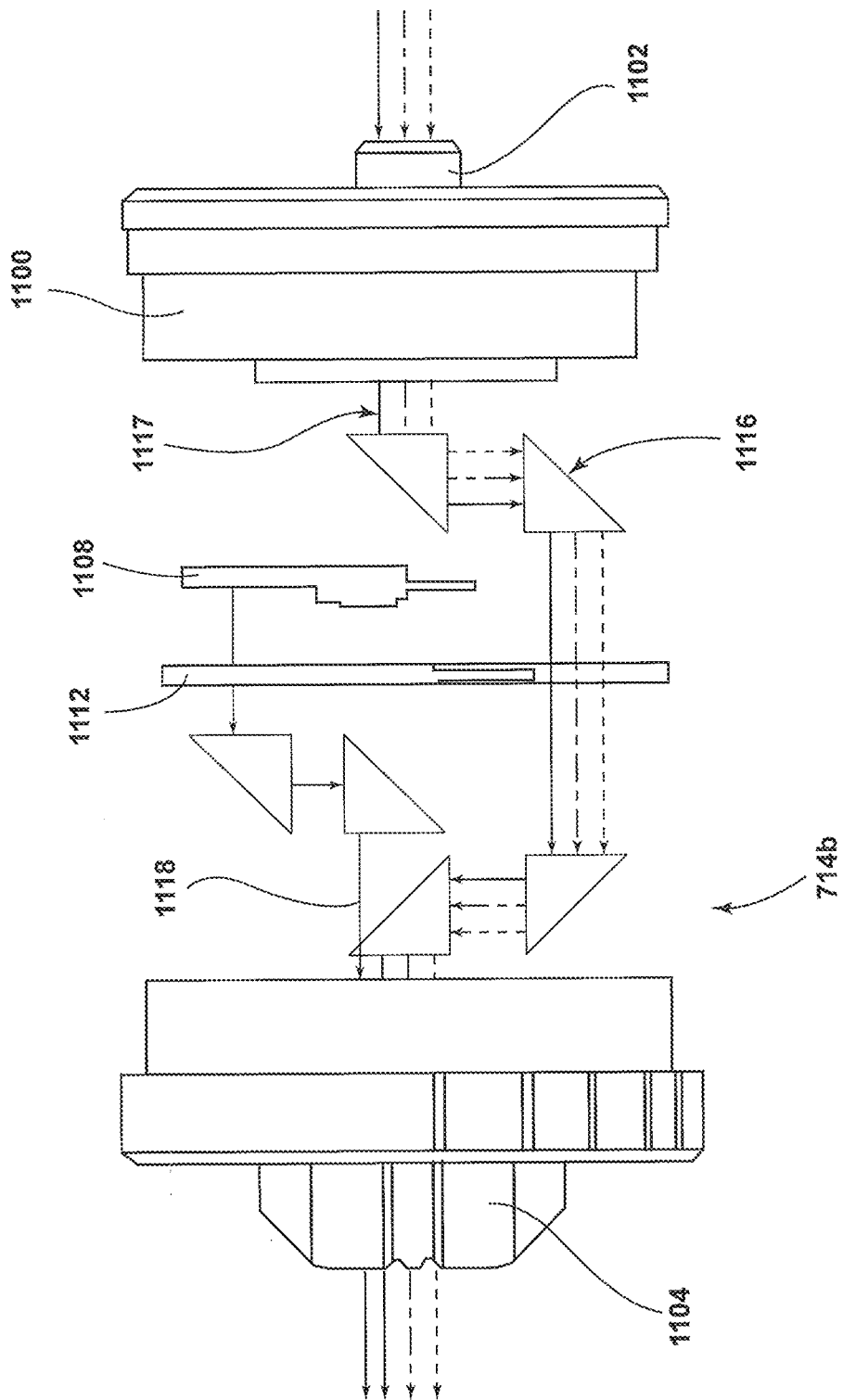
FIG. 20 is an elevational view of the modular upgrade of FIG. 18 with a portion of the housing removed, and showing the light paths therein.

Another embodiment of a light source 714 with a modular light engine 714b is depicted in FIGS. 18-20. The light source 714 includes an opening or port 714a which is shaped and sized to receive the modular light engine 714b.

The modular light engine 714b is different from that of 614b in that the modular light engine 714b does not include LED lights, but uses light from LEDs or other light sources in the light source 714 for light in the visible spectrum and/or infrared spectrum.

As depicted in FIGS. 19-20, the modular light engine 714b includes a housing 1100, a light input 1102, and a light output 1104. Inside the housing 1100 are a battery pack 1106, which may be of the rechargeable type, a UV LED chip board 1108 which is capable of providing UV light via an LED, and a microcontroller 1110 for controlling the UV LED chip board 1108. Also included within the housing 1100 are a color filter wheel 1112, a motor 1114 for turning the color filter wheel 1112 when desired, and a variety of optical prism blocks 1116 for providing light paths for the various light inputted into and generated by the modular light engine 714b.

FIG. 20 shows the various light paths for the light which may be emitted by the modular light engine 714b. Specifically, as shown, red, blue, and green light may be inputted via light input 1102 and follow along the light path 1117 as shown in FIG. 20, including through one or more of the prism blocks 1116, and to and through a portion of the filter wheel 1112. In addition, the light path 1118 for UV light generated by the UV LED chip board 1108 is depicted in FIG. 20. As shown, the UV light travels from the chip board 1108, to and through a portion of the filter wheel 1112, and to and through one or more of the prism blocks 1116 before exiting via the light output 1104.

Figure 21:
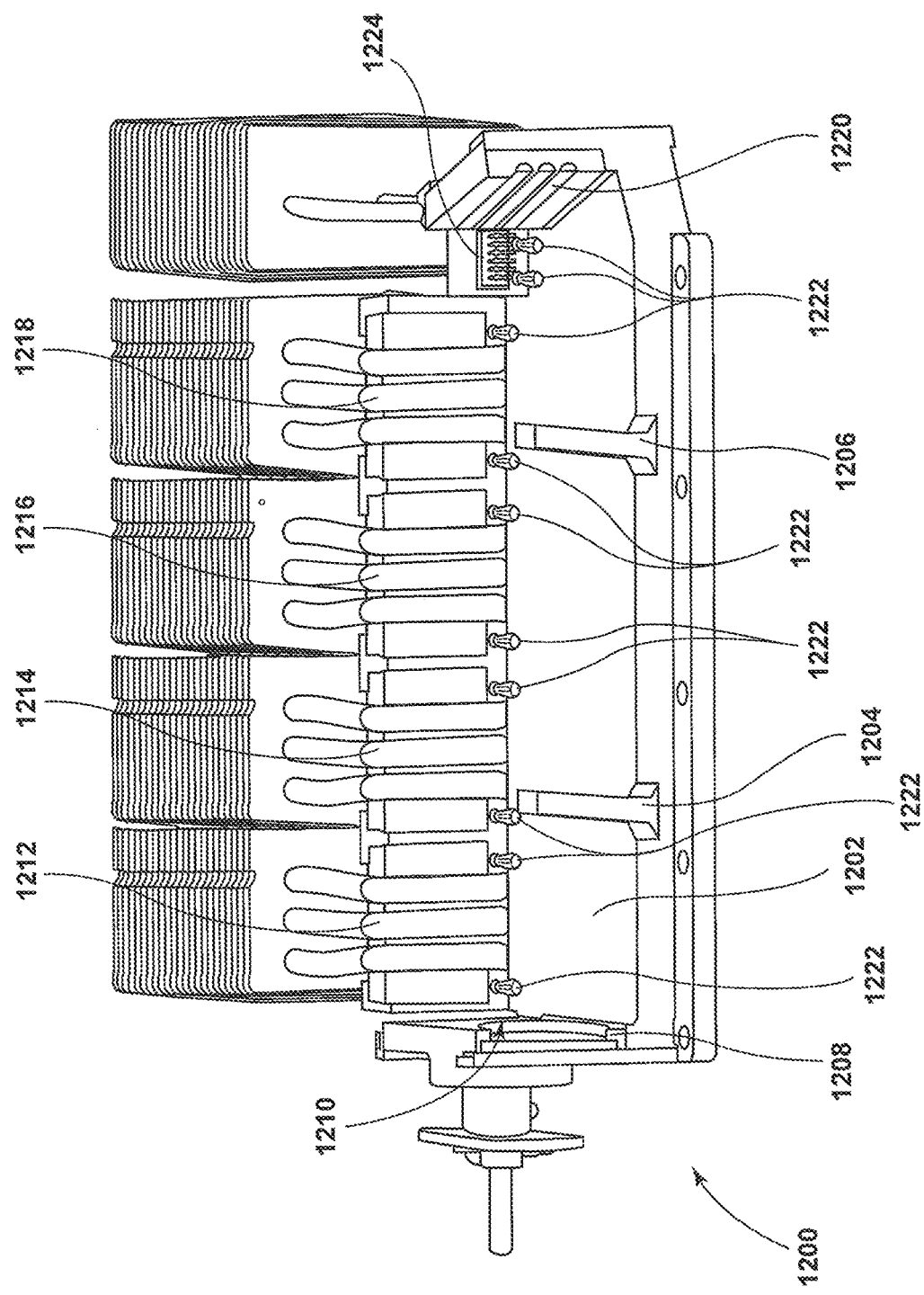
FIG. 21 is a top perspective view of a light module receiving base of a light source.
Figure 22:
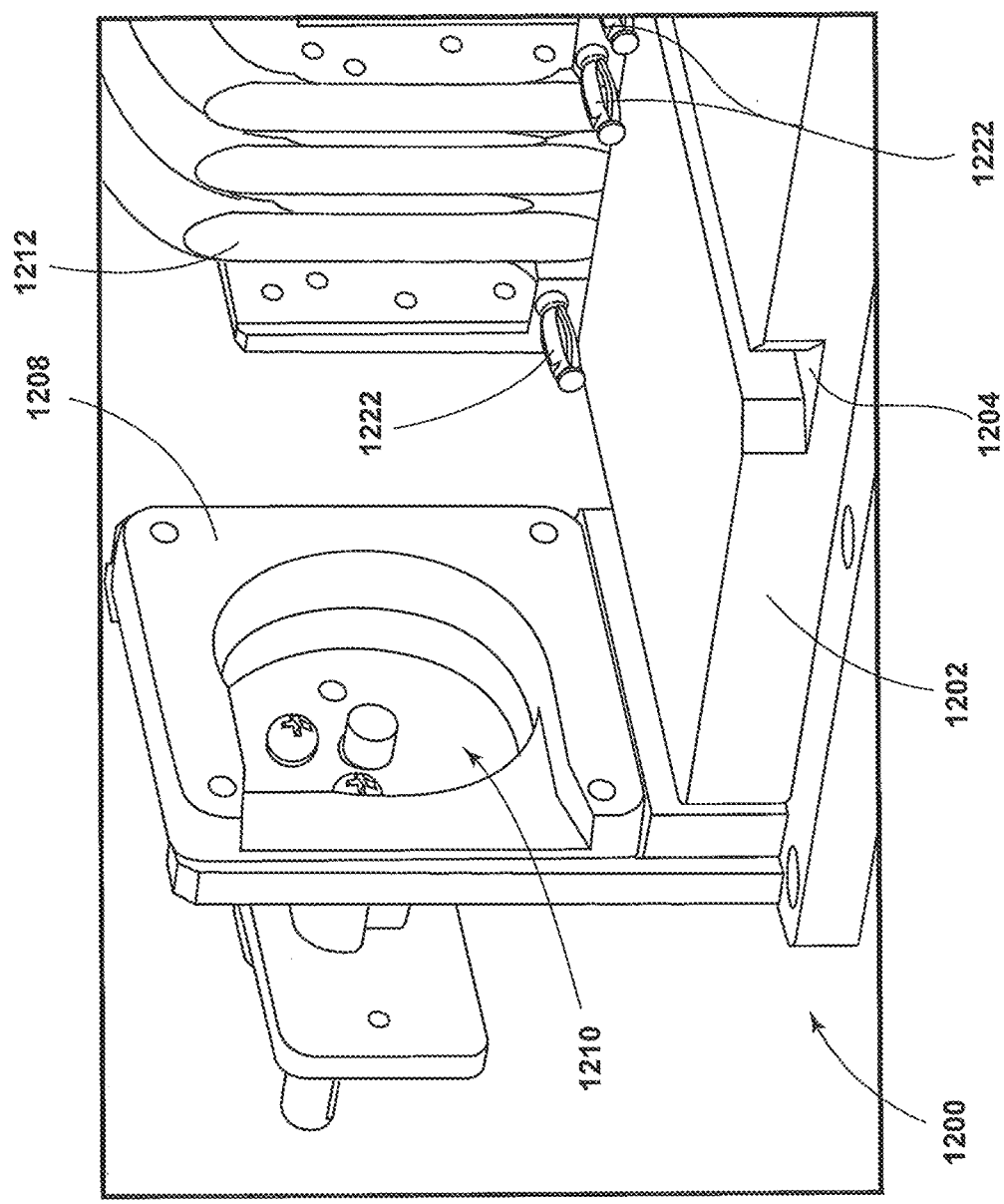
FIG. 22 is a perspective view of a portion of the light module receiving base of FIG. 21.

FIGS. 21-22 depict a light engine port 1200 which may be part of a light engine such as light source 614 and is configured to receive and connect to a light module such as light module 614b. The port 1200 includes a floor 1202 which has two slots 1204, 1206 therein for easy centering and alignment of a light module. The port 1200 also includes a substantially vertically oriented receiving member 1208 which has a groove 1210 therein that is sized to receive a portion of a front panel of a light module.

The port 1200 also includes multiple heat sinks 1212, 1214, 1216, 1218, 1220 which are sized and positioned to contact a thermal interface of an LED chip board on a light module. The heat sinks 1212, 1214, 1216, 1218, 1220 allow thermal management of the light source, including a light module via forced air cooling, while allowing the light module to be removable.

The port 1200 also preferably includes multiple high current power supply connectors, such as banana plugs 1222, for connection to a light module. In addition, an electrical pinout block 1224 is included to provide power and electronic communication to any sensors, motors, or other components that are part of the light module.

The groove 1210 in the receiving member 1208 is generally semicircular in shape with a circular indentation and is therefore shaped and sized to receive a circular portion of the end plate of a light module.

Figure 23:
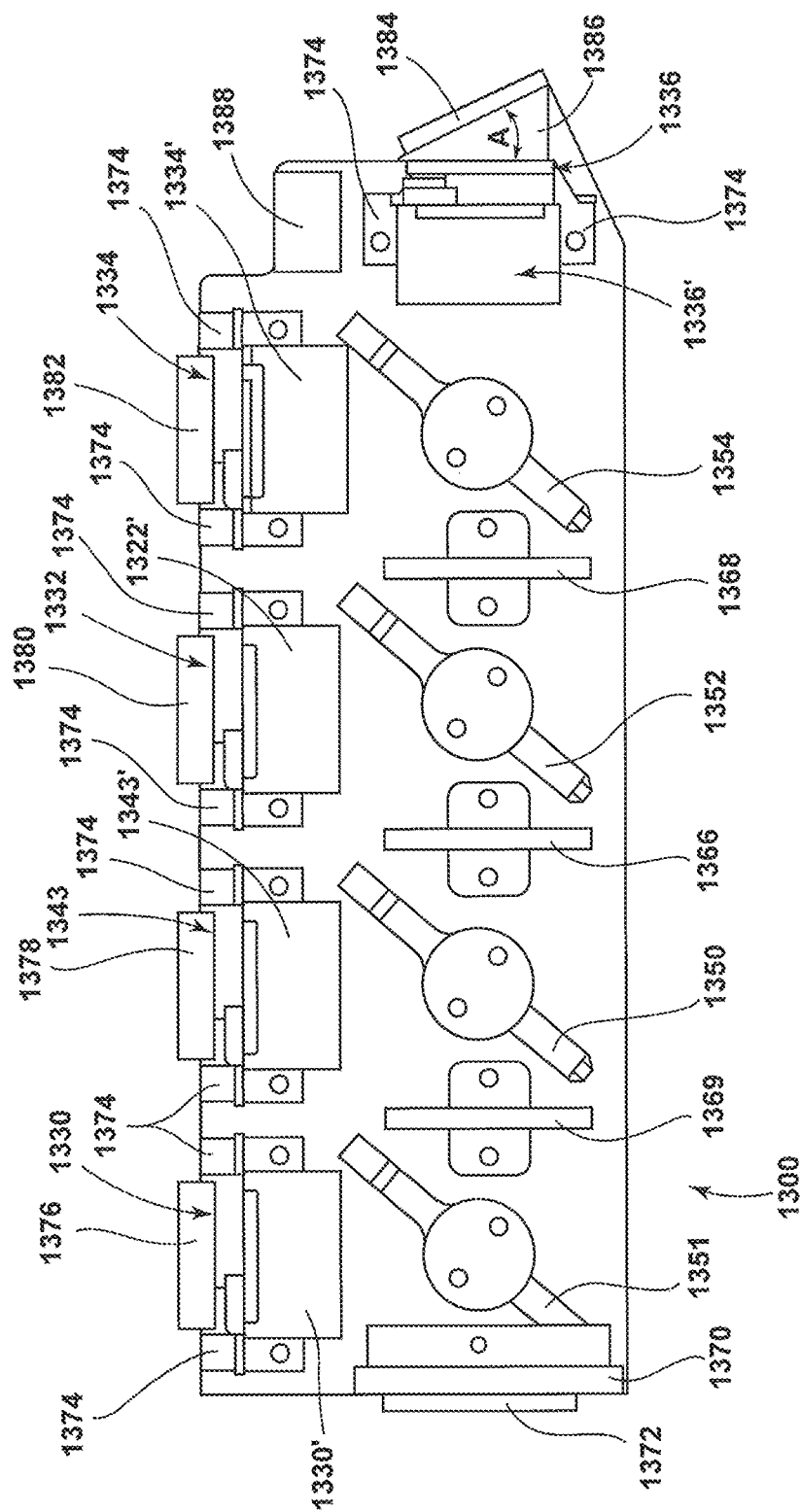
FIG. 23 is a top plan view of an embodiment of a light module.

The reference numeral 1300 (FIGS. 23-24) generally designates another embodiment of a light module of the present invention. Since light module 1300 is similar to previously described light module 614b, similar parts appearing in FIGS. 17 and 23-24, respectively, are represented by the same, corresponding number, except for the addition of 700 in the numerals of the latter. The light module 1300 includes a front panel 1370 which has a light port therein defined by a round outer lip 1372. The outer lip 1372 is sized and shaped to fit within and be received by the groove 1210 in the receiving member 1208. The LEDs and laser diode 1330, 1332, 1334, 1336, and 1343 each have preferably two power receiving ports 1374 configured to receive and engage with banana plug connectors such as the banana plug connectors 1222 of the port 1200. In addition, each of the LEDs and the laser diode has a thermal interface for conveying heat to a heat sink for that particular LED or laser diode. The LED 1330 has a thermal interface 1376 which is sized and configured to engage with the heat sink 1212 of the base 1200, the LED 1343 includes a thermal interface 1378 which is sized and configured to engage with the heat sink 1214, the LED 1332 has a thermal interface 1380 which is sized and configured to engage with the heat sink 1216, the LED 1334 has a thermal interface 1382 which is sized and configured to engage with the heat sink 1218, and the LED 1336 has a thermal interface 1384 which is sized and configured to engage with the heat sink 1220. The thermal interface 1384 is at an angle "A" with respect to the longitudinal axis of the LED 1336, as shown in FIG. 23. Angling of the thermal interface 1384, as well as the face of its respective heat sink 1220 creates an increased compression between the two to maintain heat transfer away from the LED light source. Angle A is preferably between about 20° and about 30°, and more preferably is about 25°. A wedge 1386 is placed between the thermal interface 1384 and the LED 1336 and is preferably of a material that is a good heat conductor, such as copper.

The light module 1300 also includes a pinout block (female) receiver 1388 for receiving electrical power from the port 1200, which may be used for a variety of purposes, including movement of one or more filters during the operation of the light source.

Figure 24:
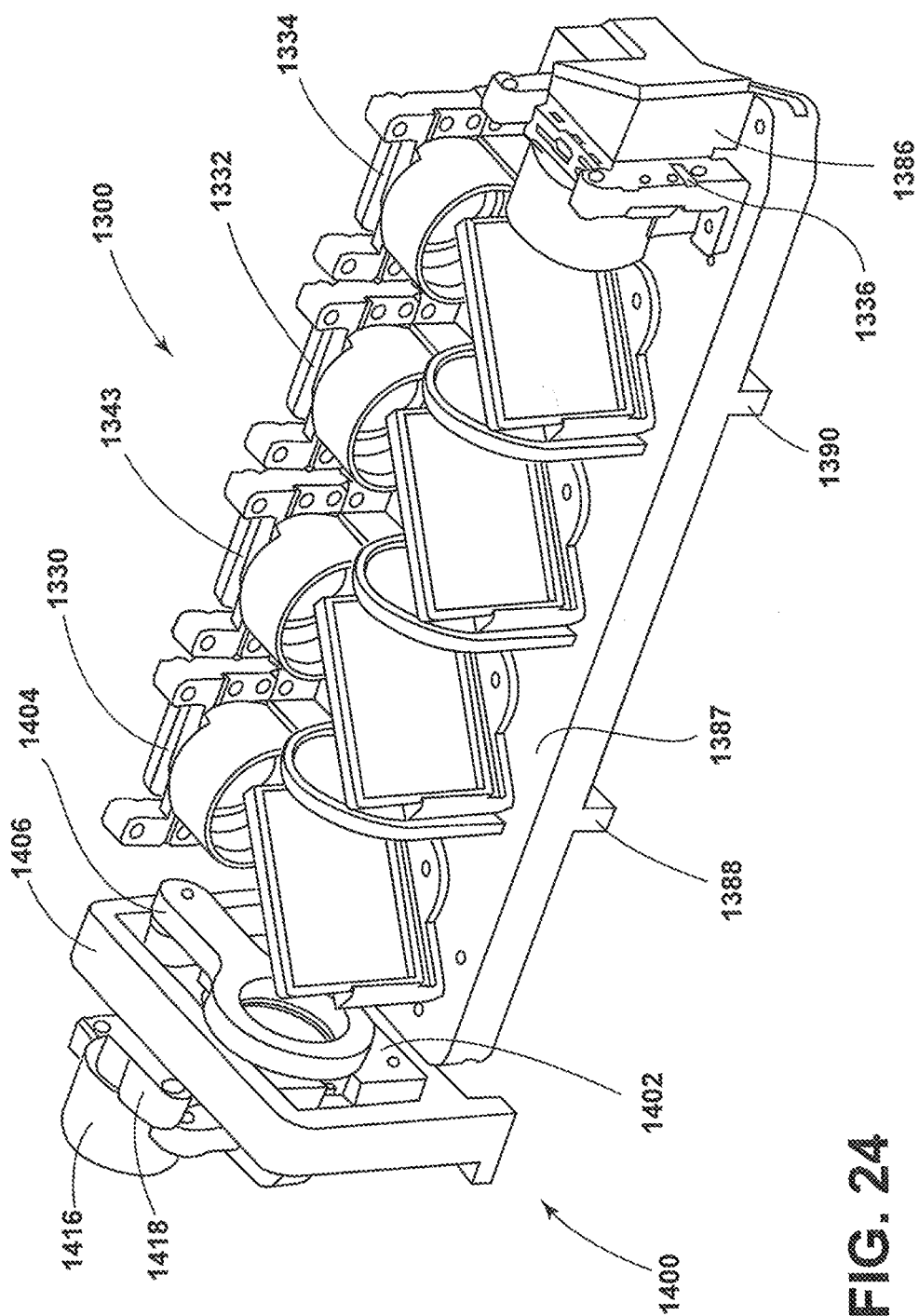
FIG. 24 is a top perspective view of the light module of FIG. 23.

As depicted in FIG. 24, the light module 1300 preferably has a base 1387 with two feet 1388, 1390 depending therefrom. The feet 1388, 1390 are spaced apart from each other and are sized and shaped to fit within grooves 1204 and 1206, respectively.

Figure 25:
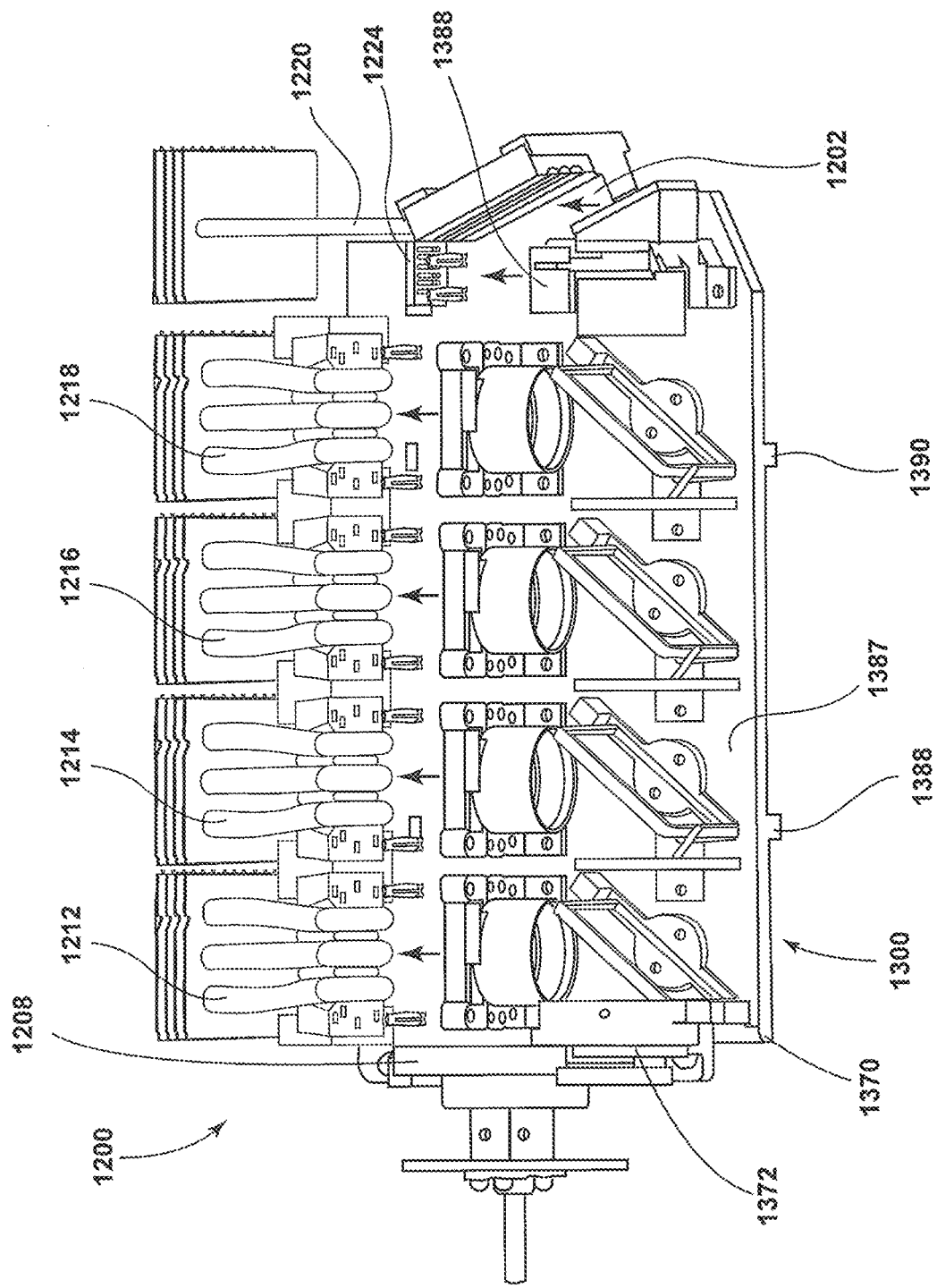
FIG. 25 is a top perspective view of the light module of FIG. 23 engaging with the base of FIG. 21.

FIG. 25 depicts the beginning of engagement between the light module 1300 and the port 1200. The straight arrows in FIG. 25 show the direction of movement of the light module 1300, once feet 1388, 1390 are aligned with and guided into the grooves 1204, 1206, respectively, for the light module 1300 to be fully connected and engaged with the port 1200.

Figure 26:
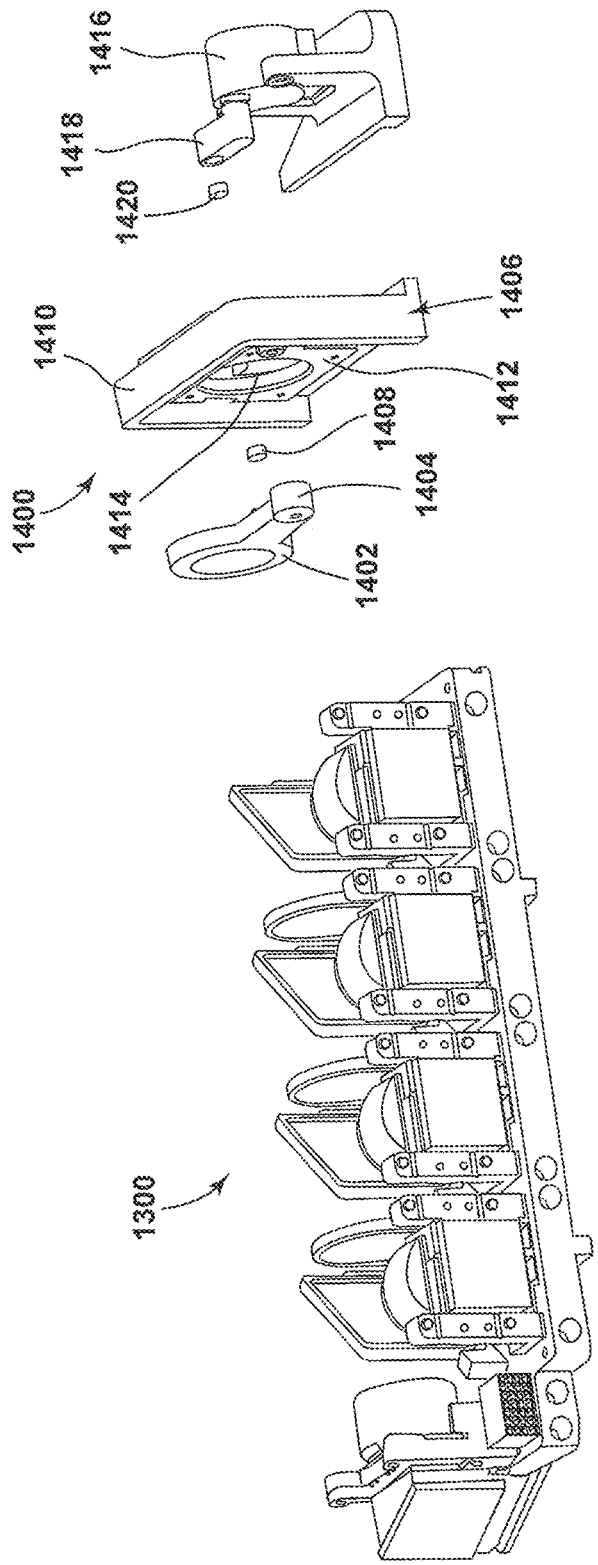
FIG. 26 is a partially exploded view of an embodiment of a light module and a movable filter.

The light source, including the port 1200, the light module 1300, or preferably a combination of the two, may include a motorized magnetically driven optical filter, which is shown in FIGS. 24 and 26. The magnetically driven optical filter device 1400 includes a movable driven filter 1402 which includes a filter arm 1404. The filter arm 1404 is attached at its distal end to a front panel 1406 and a magnet 1408.

The front panel 1406 includes a frame 1410 and an inner member 1412 attached to the frame 1410. The inner member 1412 has an aperture 1414 therein which may or may not include a lens.

On the side of the front panel 1406 opposite the filter 1402 is a motor 1416. The motor 1416 may receive electrical power from the pin 1224 of the base 1200 via the pin receiving 1388. The motor 1416 drives a lever arm 1418 which is attached to a magnet 1420.

In operation, the motor 1416 may be used to move the lever arm 1418 in a counterclockwise or clockwise direction, thereby moving the magnet 1420 with it. Due to magnetic forces, the magnet 1408 is moved along with magnet 1420, which in turn moves the filter arm 1404 and the filter 1402 in a clockwise or counterclockwise direction to move the filter 1402 into or out of the light path of the light exiting the light module 1300.

The above-described light sources and light source engines provide a flexible system by which various modes of light output can be achieved for a variety of different medical procedures. The modularity of the modular light engines gives the potential of using a variety of different modular pieces without having to purchase a whole new light source system, while providing increased capability as well as the potential for future modular components which may be used with existing light sources.

Although particular preferred embodiments of the invention have been disclosed in detail for illustrative purposes, it will be recognized that variations or modifications of the disclosed apparatus, including the rearrangement of parts, lie within the scope of the present invention.

The invention claimed is:

1. A light source system comprising:
a light source component comprising a port sized and shaped for receiving a first light module and having at least one member therein with a groove for receiving a part of the first light module;
the first light module having at least one light therein and a flange for engagement with the groove of the light source component;
the first light module being capable of being inserted into and removed from the port, the light source component and the first light module together providing a light engine for providing light to a surgical site;
the first light module being interchangeable with at least a second light module configured for generating different light than the first light module.

2. The light source system of claim 1, wherein the light source component comprises at least one heat sink, and the first light module comprises a thermal interface adjacent to the at least one light, the thermal interface engaging the at least one heat sink when the first light module is inserted into the port.

3. The light source system of claim 2, wherein the thermal interface is at an angle of between about 20° and about 30° with respect to a longitudinal axis of the at least one light.

4. The light source system of claim 2, wherein the first light module comprises a wedge between the thermal interface and the at least one light.

5. The light source system of claim 4, wherein the wedge comprises a thermally conductive material.

6. The light source system of claim 1, wherein the light engine is configured to provide white light.

7. The light source system of claim 1, wherein the light engine is configured to provide ultraviolet light.

8. The light source system of claim 1, wherein the at least one light comprises an LED.

9. The light source system of claim 1, wherein the at least one light comprises an infrared laser diode.

10. The light source system of claim 1, wherein the first light module comprises at least one lens.

11. The light source system of claim 1, wherein the first light module comprises at least one filter.

12. The light source system of claim 1, wherein the first light module comprises a receiver configured for receiving electrical power from the port.

13. The light source system of claim 1 comprising a magnetically-driven optical filter device, wherein the magnetically-driven optical filter device comprises:

a filter;
a filter arm connected at a proximal end to the filter and connected at a distal end to a first magnet; and
a motor configured to drive a lever arm comprising a second magnet, wherein driving the lever arm comprising the second magnet causes the filter arm connected to the first magnet to move the filter.

14. The light source system of claim 13, wherein moving the filter comprises moving the filter into a path of light generated by the first light module.

15. The light source system of claim 13, wherein moving the filter comprises moving the filter out of a path of light generated by the first light module.

16. The light source system of claim 13, wherein the filter arm is connected to a panel comprising an aperture.

17. The light source system of claim 16, wherein the aperture comprises a lens.

18. The light source system of claim 16, wherein the motor is located on a side of the panel opposite the filter arm.

* * * * *